United States Patent
Reihani et al.

(10) Patent No.: US 9,771,620 B2
(45) Date of Patent: Sep. 26, 2017

(54) BIOMARKERS OF HIGH-GRADE SEROUS OVARIAN CARCINOMAS

(71) Applicant: Duke University, Durham, NC (US)

(72) Inventors: Sharareh Reihani, Chapel Hill, NC (US); Angeles Alvarez Secord, Durham, NC (US); Mark Dewhirst, Chapel Hill, NC (US); Chen Jiang, Durham, NC (US); Kouros Owzar, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/282,603

(22) Filed: May 20, 2014

(65) Prior Publication Data
US 2014/0342929 A1 Nov. 20, 2014

Related U.S. Application Data

(60) Provisional application No. 61/825,189, filed on May 20, 2013, provisional application No. 61/867,219, filed on Aug. 19, 2013.

(51) Int. Cl.
*C12Q 1/68* (2006.01)
(52) U.S. Cl.
CPC ...... *C12Q 1/6886* (2013.01); *C12Q 2600/118* (2013.01); *C12Q 2600/158* (2013.01)
(58) Field of Classification Search
None
See application file for complete search history.

(56) References Cited

PUBLICATIONS

Bonome et al. (2008) A Gene Signature Predicting for Survival in Suboptimally Debulked Patients with Ovarian Cancer. Cancer Research, 68(13):5478-5486.*
Whitehead et al. (2005) Variation in tissue-specific gene expression among natural populations. Genome Biology, 6:R13.*
Ross et al. (2000) Systematic variation in gene expression patterns in human cancer cell lines. Nature Genetics, 24:227-235.*
Lin et al. (2009) Deep depletion of abundant serum proteins reveals low-abundant proteins as potential biomarkers for human ovarian cancer. Proteomics Clinical Applications, 3:853-861.*
Slonim, D. (2002) From patterns to pathways: gene expression data analysis comes of age. Nature Genetics Supplement, 32:502-508.*
Wu et al. (2006) The prognostic impact of EphB2/B4 expression on patients with advanced ovarian carcinoma. Gynecologic Oncology, 102:15-21.*
Berchuck et al. (2005) Patterns of Gene ExpressionThat Characterize Long-term Survival in Advanced Stage Serous Ovarian Cancers. Clinical Cancer Research, 11(10):3686-3696.*
Affymetrix HG-U133A Annotation File (filtered excerpt, obtained from <http://www.affymetrix.com/Auth/analysis/downloads/na35/ivt/HG-U133A.na35.annot.csv.zip> on Apr. 29, 2016, 1 page).*
Maksimova, N., K. Hara, A. Miyashia, I. Nikolaeva, A. Shiga, A. Nogovicina, A. Sukhomyasova, V. Argunov, A. Shvedova, T. Ikeuchi, M. Nishizawa, R. Kuwano and O. Onodera (2007). "Clinical, molecular and histopathological features of short stature syndrome with novel CUL7 mutation in Yakuts: new population isolate in Asia." J Med Genet 44(12): 772-778.
May, K. E., J. Villar, S. Kirtley, S. H. Kennedy and C. M. Becker (2011). "Endometrial alterations in endometriosis: a systematic review of putative biomarkers." Hum Reprod Update 17(5): 637-653.
Miyazaki, T., H. Kato, M. Fukuchi, M. Nakajima and H. Kuwano (2003). "EphA2 overexpression correlates with poor prognosis in esophageal squamous cell carcinoma." Int J Cancer 103(5): 657-663.
Mok SC, Bonome T, Vathipadiekal V, Bell A, Johnson ME, et al. (2009) A gene signature predictive for outcome in advanced ovarian cancer identifies a survival factor: microfibril-associated glycoprotein 2. Cancer Cell 16: 521-532.
Monk BJ PA, Vergote I, (2013) A phase III, randomized, double-blind trial of weekly paclitaxel plus the angiopoietin 1 and 2 inhibitor, trebananib, or placebo in women with recurrent ovarian cancer: TRINOVA-1. . European Cancer Congress 2013 (ECCO-ESMO-ESTRO);Sep. 27-Oct. 1, 2013; Amsterdam, The Netherlands Abstract LBA41.
Morishige, K., H. Kurachi, K. Amemiya, H. Adachi, M. Inoue, A. Miyake, O. Tanizawa and Y. Sakoyama (1991). "Involvement of transforming growth factor alpha/epidermal growth factor receptor autocrine growth mechanism in an ovarian cancer cell line in vitro." Cancer Res 51(21): 5951-5955.
Naina HV, Harris S (2012) Paraneoplastic thrombocytosis in ovarian cancer. N Engl J Med 366: 1840; author reply 1840.
Nie XC, Wang JP, Zhu W, Xu XY, Xing YN, et al. (2013) COL4A3 expression correlates with pathogenesis, pathologic behaviors, and prognosis of gastric carcinomas. Hum Pathol 44: 77-86.
Nowsheen, S., T. Cooper, J. A. Bonner, A. F. LoBuglio and E. S. Yang (2012). "HER2 overexpression renders human breast cancers sensitive to PARP inhibition independently of any defect in homologous recombination DNA repair." Cancer Res 72(18): 4796-4806.
Owzar K, Barry WT, Jung SH (2011) Statistical Considerations for Analysis of Microarray Experiments. Cts-Clinical and Translational Science 4: 466-477.
Palagani, V., M. El Khatib, U. Kossatz, P. Bozko, M. R. Muller, M. P. Manns, T. Krech, N. P. Malek and R. R. Plentz (2012). "Epithelial mesenchymal transition and pancreatic tumor initiating CD44+/EpCAM+ cells are inhibited by gamma-secretase inhibitor IX." Plos One 7(10): e46514.
Perren, T., A. M. Swart, J. Pfisterer, J. Ledermann, A. Lortholary, G. Kristensen, M. Carey, P. Beale, A. Cervantes, A. Oza and G. I. Collaborators (2010). "Icon7: A Phase Iii Randomised Gynaecologic Cancer Intergroup Trial of Concurrent Bevacizumab and Chemotherapy Followed by Maintenance Bevacizumab, Versus Chemotherapy Alone in Women with Newly Diagnosed Epithelial Ovarian (Eoc), Primary Peritoneal (Ppc) or Fallopian Tube Cancer (Ftc)." Annals of Oncology 21: 2-3.

(Continued)

*Primary Examiner* — Neil P Hammell
(74) *Attorney, Agent, or Firm* — NK Patent Law, PLLC

(57) ABSTRACT

The present disclosure provides biomarkers useful for determining the prognosis of conditions such as ovarian cancer. The presently disclosed subject matter provides angiogenic biomarkers and methods and compositions for predicting overall survival (OS) in women with high-grade serous carcinomas (HGSCs). The presently disclosed subject matter provides compositions and methods that enable rationally directed therapies to improve outcome in women with HGSC.

4 Claims, 15 Drawing Sheets

(56) References Cited

PUBLICATIONS

Pino, M. S., M. Shrader, C. H. Baker, F. Cognetti, H. Q. Xiong, J. L. Abbruzzese and D. J. McConkey (2006). "Transforming growth factor alpha expression drives constitutive epidermal growth factor receptor pathway activation and sensitivity to gefitinib (Iressa) in human pancreatic cancer cell lines." Cancer Res 66(7): 3802-3812.
Randall LM, Monk BJ (2010) Bevacizumab toxicities and their management in ovarian cancer. Gynecol Oncol 117: 497-504.
Rubatt, J. M., K. M. Darcy, A. Hutson, S. M. Bean, L. J. Havrilesky, L. A. Grace, A. Berchuck and A. A. Secord (2009). "Independent prognostic relevance of microvessel density in advanced epithelial ovarian cancer and associations between CD31, CD105, p53 status, and angiogenic marker expression: A Gynecologic Oncology Group study." Gynecol Oncol 112(3): 469-474.
Saharinen, P., K. Kerkela, N. Ekman, M. Marron, N. Brindle, G. M. Lee, H. Augustin, G. Y. Koh and K. Alitalo (2005). "Multiple angiopoietin recombinant proteins activate the Tie1 receptor tyrosine kinase and promote its interaction with Tie2." J Cell Biol 169(2): 239-243.
Schwartz, J. D., E. K. Rowinsky, H. Youssoufian, B. Pytowski and Y. Wu (2010). "Vascular endothelial growth factor receptor-1 in human cancer: concise review and rationale for development of IMC-18F1 (Human antibody targeting vascular endothelial growth factor receptor-1)." Cancer 116(4 Suppl): 1027-1032.
Shibuya, M. (2006). "Vascular endothelial growth factor receptor-1 (VEGFR-1/Flt-1): a dual regulator for angiogenesis." Angiogenesis 9(4): 225-230; discussion 231.
Singh, H., T. A. Tahir, D. O. Alawo, E. Issa and N. P. Brindle (2011). "Molecular control of angiopoietin signalling." Biochem Soc Trans 39(6): 1592-1596.
Slamon, D. J., B. Leyland-Jones, S. Shak, H. Fuchs, V. Paton, A. Bajamonde, T. Fleming, W. Eiermann, J. Wolter, M. Pegram, J. Baselga and L. Norton (2001). "Use of chemotherapy plus a monoclonal antibody against HER2 for metastatic breast cancer that overexpresses HER2." New England Journal of Medicine 344(11): 783-792.
Slungaard, A. (2005). "Platelet factor 4: a chemokine enigma." Int J Biochem Cell Biol 37(6): 1162-1167.
Stone RL, Sood AK, Coleman RL (2010) Collateral damage: toxic effects of targeted antiangiogenic therapies in ovarian cancer. Lancet Oncol 11: 465-475.
Stone RL, Nick AM, McNeish IA, Balkwill F, Han HD, et al. (2012) Paraneoplastic thrombocytosis in ovarian cancer. N Engl J Med 366: 610-618.
Sun, M., G. Wang, J. E. Paciga, R. I. Feldman, Z. Q. Yuan, X. L. Ma, S. A. Shelley, R. Jove, P. N. Tsichlis, S. V. Nicosia and J. Q. Cheng (2001). "AKT1/PKB alpha kinase is frequently elevated in human cancers and its constitutive activation is required for oncogenic transformation in NIH3T3 cells." American Journal of Pathology 159(2): 431-437.
Takai, N., T. Miyazaki, K. Fujisawa, K. Nasu and I. Miyakawa (2001). "Expression of receptor tyrosine kinase EphB4 and its ligand ephrin-B2 is associated with malignant potential in endometrial cancer." Oncol Rep 8(3): 567-573.
Teoh, D. and A. A. Secord (2012). "Antiangiogenic agents in combination with chemotherapy for the treatment of epithelial ovarian cancer." Int J Gynecol Cancer 22(3): 348-359.
Tuzi, N. L. and W. J. Gullick (1994). "Eph, the Largest Known Family of Putative Growth-Factor Receptors." British Journal of Cancer 69(3): 417-421.
Wang, Z. and H. Huang (2013). "Platelet factor-4 (CXCL4/PF-4): An angiostatic chemokine for cancer therapy." Cancer Lett.
Wei, K. C., C. Y. Huang, P. Y. Chen, L. Y. Feng, T. W. Wu, S. M. Chen, H. C. Tsai, Y. J. Lu, N. M. Tsang, C. K. Tseng, P. C. Pai and J. W. Shin (2010). "Evaluation of the prognostic value of CD44 in glioblastoma multiforme." Anticancer Res 30(1): 253-259.
Weidner, N., P. R. Carroll, J. Flax, W. Blumenfeld and J. Folkman (1993). "Tumor angiogenesis correlates with metastasis in invasive prostate carcinoma." Am J Pathol 143(2): 401-409.
Weidner, N., J. Folkman, F. Pozza, P. Bevilacqua, E. N. Allred, D. H. Moore, S. Meli and G. Gasparini (1992). "Tumor angiogenesis: a new significant and independent prognostic indicator in early-stage breast carcinoma." J Natl Cancer Inst 84(24): 1875-1887.
Weidner, N., J. P. Semple, W. R. Welch and J. Folkman (1991). "Tumor angiogenesis and metastasis—correlation in invasive breast carcinoma." N Engl J Med 324(1): 1-8.
Wu, Q., Z. Suo, G. B. Kristensen, M. Baekelandt and J. M. Nesland (2006). "The prognostic impact of EphB2/B4 expression on patients with advanced ovarian carcinoma." Gynecologic Oncology 102(1): 15-21.
Wu, W., M. S. O'Reilly, R. R. Langley, R. Z. Tsan, C. H. Baker, N. Bekele, X. M. Tang, A. Onn, I. J. Fidler and R. S. Herbst (2007). "Expression of epidermal growth factor (EGF)/transforming growth factor-alpha by human lung cancer cells determines their response to EGF receptor tyrosine kinase inhibition in the lungs of mice." Mol Cancer Ther 6(10): 2652-2663.
Yoshihara K, Tajima A, Yahata T, Kodama S, Fujiwara H, et al. (2010) Gene expression profile for predicting survival in advanced-stage serous ovarian cancer across two independent datasets. PLoS One 5: e9615.
Zatterstrom, U. K., E. Brun, R. Willen, E. Kjellen and J. Wennerberg (1995). "Tumor angiogenesis and prognosis in squamous cell carcinoma of the head and neck." Head Neck 17(4): 312-318.
Zhang, S., C. Balch, M. W. Chan, H. C. Lai, D. Matei, J. M. Schilder, P. S. Yan, T. H. Huang and K. P. Nephew (2008). "Identification and characterization of ovarian cancer-initiating cells from primary human tumors." Cancer Res 68(11): 4311-4320.
Zhao, D., F. Zhang, W. Zhang, J. He, Y. Zhao and J. Sun (2013). "Prognostic role of hormone receptors in ovarian cancer: a systematic review and meta-analysis." Int J Gynecol Cancer 23(1): 25-33.
Zoller, M. (2011). "CD44: can a cancer-initiating cell profit from an abundantly expressed molecule?" Nature Reviews Cancer 11(4): 254-267.
Siamakpour-Reihani, S. (2013). "Prognostic Significance of Differential Expression of Angiogenic Genes in Women with Invasive High-Grade Serous Ovarian Carcinoma." Slideshow presented at the 2013 ASCO Annual Meeting, Duke Cancer Institute, Jun. 1, 2013.
Aghajanian C, Blank SV, Goff BA, Judson PL, Teneriello MG, et al. (2012) OCEANS: a randomized, double-blind, placebo-controlled phase III trial of chemotherapy with or without bevacizumab in patients with platinum-sensitive recurrent epithelial ovarian, primary peritoneal, or fallopian tube cancer. J Clin Oncol 30: 2039-2045.
Alvarez, A. A., H. R. Krigman, R. S. Whitaker, R. K. Dodge and G. C. Rodriguez (1999). "The prognostic significance of angiogenesis in epithelial ovarian carcinoma." Clin Cancer Res 5(3): 587-591.
Arai, T., J. S. Kasper, J. R. Skaar, S. H. Ali, C. Takahashi and J. A. DeCaprio (2003). "Targeted disruption of p185/Cul7 gene results in abnormal vascular morphogenesis." Proceedings of the National Academy of Sciences 100(17): 9855-9860.
Bast, R. C., Jr., B. Hennessy and G. B. Mills (2009). "The biology of ovarian cancer: new opportunities for translation." Nature Reviews Cancer 9(6): 415-428.
Bellacosa, A., C. C. Kumar, A. D. Cristofano and J. R. Testa (2005). Activation of AKT Kinases in Cancer: Implications for Therapeutic Targeting. Advances in Cancer Research. F. V. W. George and K. George, Academic Press. vol. 94: 29-86.
Berchuck, A., E. S. Iversen, J. M. Lancaster, J. Pittman, J. Luo, P. Lee, S. Murphy, H. K. Dressman, P. G. Febbo, M. West, J. R. Nevins and J. R. Marks (2005). "Patterns of Gene Expression That Characterize Long-term Survival in Advanced Stage Serous Ovarian Cancers." Clinical Cancer Research 11(10): 3686-3696.
Berchuck, A., E. S. Iversen, J. Luo, J. P. Clarke, H. Horne, D. A. Levine, J. Boyd, M. A. Alonso, A. A. Secord, M. Q. Bernardini, J. C. Barnett, T. Boren, S. K. Murphy, H. K. Dressman, J. R. Marks and J. M. Lancaster (2009). "Microarray analysis of early stage serous ovarian cancers shows profiles predictive of favorable outcome." Clin Cancer Res 15(7): 2448-2455.

(56) References Cited

OTHER PUBLICATIONS

Berclaz, G., B. Flutsch, H. J. Altermatt, V. Rohrbach, V. Djonov, a. Ziemiecki, E. Dreher and A. C. Andres (2002). "Loss of EphB4 receptor tyrosine kinase protein expression during carcinogenesis of the human breast." Oncol Rep 9(5): 985-989.
Bentink S, Haibe-Kains B, Risch T, Fan JB, Hirsch MS, et al. (2012) Angiogenic mRNA and microRNA gene expression signature predicts a novel subtype of serous ovarian cancer. PLoS One 7: e30269.
Bojesen, S. E., S. K. Kjaer, E. V. Hogdall, B. L. Thomsen, C. K. Hogdall, J. Blaakaer, A. Tybjaerg-Hansen and B. G. Nordestgaard (2005). "Increased risk of ovarian cancer in integrin beta3 Leu33Pro homozygotes." Endocr Relat Cancer 12(4): 945-952.
Bolstad, B. M., R. A. Irizarry, M. Astrand and T. P. Speed (2003). "A comparison of normalization methods for high density oligonucleotide array data based on variance and bias." Bioinformatics 19(2): 185-193.
Bonome T, Levine DA, Shih J, Randonovich M, Pise-Masison CA, et al. (2008) A gene signature predicting for survival in suboptimally debulked patients with ovarian cancer. Cancer Res 68: 5478-5486.
Bookman MA, Darcy KM, Clarke-Pearson D, Boothby RA, Horowitz IR (2003) Evaluation of monoclonal humanized anti-HER2 antibody, trastuzumab, in patients with recurrent or refractory ovarian or primary peritoneal carcinoma with overexpression of HER2: a phase II trial of the Gynecologic Oncology Group. J Clin Oncol 21: 283-290.
Bose, S., S. Chandran, J. M. Mirocha and N. Bose (2005). "The Akt pathway in human breast cancer: a tissue-array-based analysis." Mod Pathol 19(2): 238-245.
Burger, R. A. (2007). "Experience with bevacizumab in the management of epithelial ovarian cancer." J Clin Oncol 25(20): 2902-2908.
Burger, R. A. (2011). "Antiangiogenic agents should be integrated into the standard treatment for patients with ovarian cancer." Ann Oncol 22 Suppl 8: viii65-viii68.
Camenisch G, Pisabarro MT, Sherman D, Kowalski J, Nagel M, et al. (2002) ANGPTL3 stimulates endothelial cell adhesion and migration via integrin alpha vbeta 3 and induces blood vessel formation in vivo. J Biol Chem 277: 17281-17290.
Cancer Genome Atlas Research N (2011) Integrated genomic analyses of ovarian carcinoma. Nature 474: 609-615.
Cheng, J. Q., A. K. Godwin, A. Bellacosa, T. Taguchi, T. F. Franke, T. C. Hamilton, P. N. Tsichlis and J. R. Testa (1992). "AKT2, a putative oncogene encoding a member of a subfamily of protein-serine/threonine kinases, is amplified in human ovarian carcinomas." Proc Natl Acad Sci U S A 89(19): 9267-9271.
Collins, A. T., P. A. Berry, C. Hyde, M. J. Stower and N. J. Maitland (2005). "Prospective identification of tumorigenic prostate cancer stem cells." Cancer Res 65(23): 10946-10951.
Combaret, V., C. Lasset, D. Frappaz, R. Bouvier, P. Thiesse, A. C. Rebillard, T. Philip and M. C. Favrot (1995). "Evaluation of CD44 prognostic value in neuroblastoma: Comparison with the other prognostic factors." European Journal of Cancer 31(4): 545-549.
Crowell JA, Steele VE, Fay JR (2007) Targeting the AKT protein kinase for cancer chemoprevention. Mol Cancer Ther 6: 2139-2148.
Dalerba, P., S. J. Dylla, I. K. Park, R. Liu, X. Wang, R. W. Cho, T. Hoey, A. Gurney, E. H. Huang, D. M. Simeone, A. A. Shelton, G. Parmiani, C. Castelli and M. F. Clarke (2007). "Phenotypic characterization of human colorectal cancer stem cells." Proc Natl Acad Sci U S A 104(24): 10158-10163.
de Jong, J. S., P. J. van Diest and J. P. Baak (2000). "Hot spot microvessel density and the mitotic activity index are strong additional prognostic indicators in invasive breast cancer." Histopathology 36(4): 306-312.
Denkert C, Budczies J, Darb-Esfahani S, Gyorffy B, Sehouli J, et al. (2009) A prognostic gene expression index in ovarian cancer—validation across different independent data sets. J Pathol 218: 273-280.
Derynck, R., A. B. Roberts, M. E. Winkler, E. Y. Chen and D. V. Goeddel (1984). "Human transforming growth factor-alpha: precursor structure and expression in E. coli." Cell 38(1): 287-297.

Ellis LM, Hicklin DJ (2008) VEGF-targeted therapy: mechanisms of anti-tumour activity. Nat Rev Cancer 8: 579-591.
Ellis LM (2006) The role of neuropilins in cancer. Mol Cancer Ther 5: 1099-1107.
Fillmore, C. M. and C. Kuperwasser (2008). "Human breast cancer cell lines contain stem-like cells that self-renew, give rise to phenotypically diverse progeny and survive chemotherapy." Breast Cancer Res 10(2): R25.
Folkman, J. (1994). "Angiogenesis and breast cancer." Journal of Clinical Oncology 12(3): 441-443.
Folkman, J. (2002). "Role of angiogenesis in tumor growth and metastasis." Seminars in Oncology 29(6): 15-18.
Frumovitz M, Sood AK (2007) Vascular endothelial growth factor (VEGF) pathway as a therapeutic target in gynecologic malignancies. Gynecologic Oncology 104: 768-778.
Gentleman RC, Carey VJ, Bates DM, Bolstad B, Dettling M, et al. (2004) Bioconductor: open software development for computational biology and bioinformatics. Genome Biology 5.
Georgiou GK, Igglezou M, Sainis I, Vareli K, Batsis H, et al. (2013) Impact of breast cancer surgery on angiogenesis circulating biomarkers: a prospective longitudinal study. World J Surg Oncol 11: 213.
Goel S, Gupta N, Walcott BP, Snuderl M, Kesler CT, et al. (2013) Effects of Vascular-Endothelial Protein Tyrosine Phosphatase Inhibition on Breast Cancer Vasculature and Metastatic Progression. Journal of the National Cancer Institute 105: 1188-1201.
Gottfried E. Konecny CW, et al. Prognostic relevance of gene signatures in high-grade serous ovarian carcinoma. 2013. J Clin Oncol 31, 2013.
Himanen J-P, Saha N, Nikolov DB (2007) Cell-cell signaling via Eph receptors and ephrins. Current Opinion in Cell Biology 19: 534-542.
Hiratsuka, S., Y. Maru, A. Okada, M. Seiki, T. Noda and M. Shibuya (2001). "Involvement of Flt-1 tyrosine kinase (vascular endothelial growth factor receptor-1) in pathological angiogenesis." Cancer Res 61(3): 1207-1213.
Hlatky, L., P. Hahnfeldt and J. Folkman (2002). "Clinical application of antiangiogenic therapy: microvessel density, what it does and doesn't tell us." J Natl Cancer Inst 94(12): 883-893.
Hothorn T, Hornik K, Zeileis A (2006) Unbiased recursive partitioning: A conditional inference framework. Journal of Computational and Graphical Statistics 15: 651-674.
Indumathi, S., R. Harikrishnan, J. S. Rajkumar, D. Sudarsanam and M. Dhanasekaran (2013). "Prospective biomarkers of stem cells of human endometrium and fallopian tube compared with bone marrow." Cell Tissue Res.
Jones, N., K. Iljin, D. J. Dumont and K. Alitalo (2001). "Tie receptors: new modulators of angiogenic and lymphangiogenic responses." Nat Rev Mol Cell Biol 2(4): 257-267.
Jung, P., B. Verdoodt, A. Bailey, J. R. Yates, A. Menssen and H. Hermeking (2007). "Induction of Guilin 7 by DNA damage attenuates p53 function." Proceedings of the National Academy of Sciences 104(27): 11388-11393.
Kauppila S, Saarela J, Stenback F, Risteli J, Kauppila A, et al. (1996) Expression of mRNAs for type I and type III procollagens in serous ovarian cystadenomas and cystadenocarcinomas. American Journal of Pathology 148: 539-548.
Kim, S. S., M. Shago, L. Kaustov, P. C. Boutros, J. W. Clendening, Y. Sheng, G. A. Trentin, D. Barsyte-Lovejoy, D. Y. L. Mao, R. Kay, I. Jurisica, C. H. Arrowsmith and L. Z. Penn (2007). "CUL7 Is a Novel Antiapoptotic Oncogene." Cancer Research 67(20): 9616-9622.
Kontos CD, Willett CG (2013) Inhibiting the inhibitor: targeting vascular endothelial protein tyrosine phosphatase to promote tumor vascular maturation. J Natl Cancer Inst 105: 1163-1165.
Kyama, C. M., L. Overbergh, A. Mihalyi, C. Meuleman, J. M. Mwenda, C. Mathieu and T. M. D'Hooghe (2008). "Endometrial and peritoneal expression of aromatase, cytokines, and adhesion factors in women with endometriosis." Fertil Steril 89(2): 301-310.
Lee, J. and P. Zhou (2010). "Cullins and cancer." Genes Cancer 1(7): 690-699.

(56) References Cited

OTHER PUBLICATIONS

Loges, S., Schmidt, T. and Carmeliet, P. (2010). "Mechanisms of resistance to anti-angiogenic therapy and development of third-generation anti-angiogenic drug candidates." Genes Cancer 1(1): 12-25.

Maeda, Y., T. Suzuki, X. F. Pan, G. Chen, S. Q. Pan, T. Bartman and J. A. Whitsett (2008). "CUL2 is required for the activity of hypoxia-inducible factor and vasculogenesis." Journal of Biological Chemistry 283(23): 16084-16092.

* cited by examiner

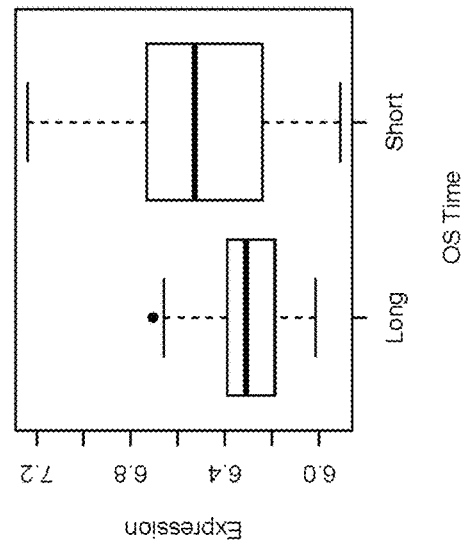
FIG. 1 AKT1 (pvalue=0.00192)
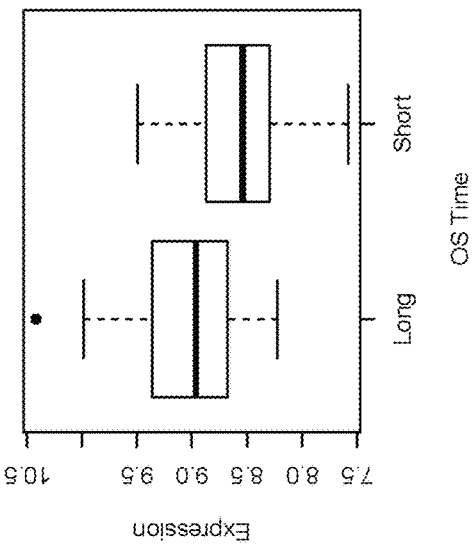
FIG. 2 ANGPT4 (pvalue=0.0374)
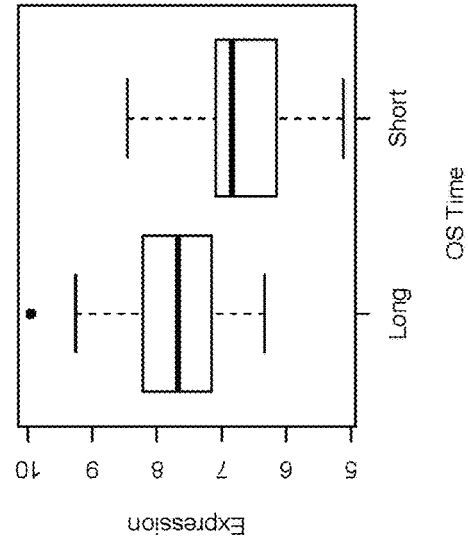
FIG. 3 ANGPTL3 (pvalue=0.00253)
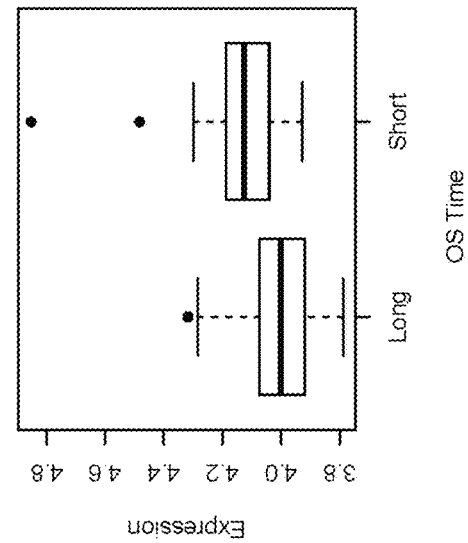
FIG. 4 CD44 (pvalue=6.49e-05)

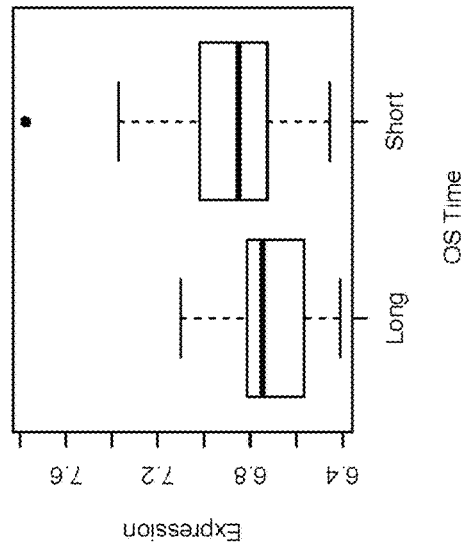
FIG. 5 COL4A3 (pvalue=0.0194)
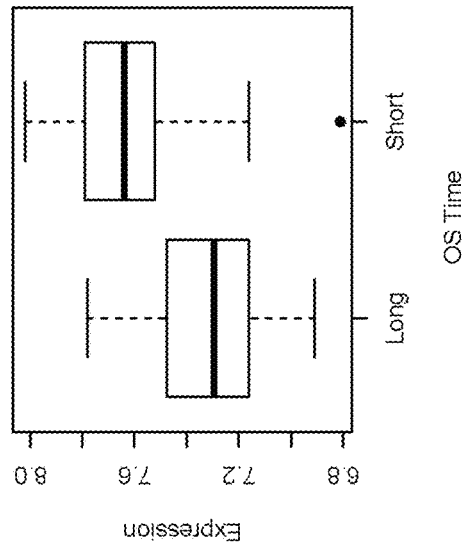
FIG. 6 CSF3 (pvalue=0.00747)
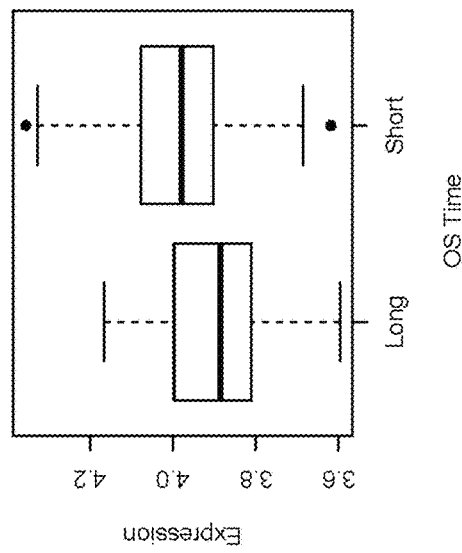
FIG. 7 CUL7 (pvalue=0.000223)
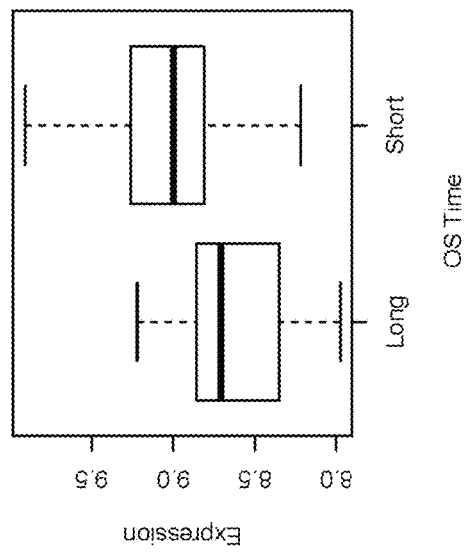
FIG. 8 EPHB2 (pvalue=4.4e-05)

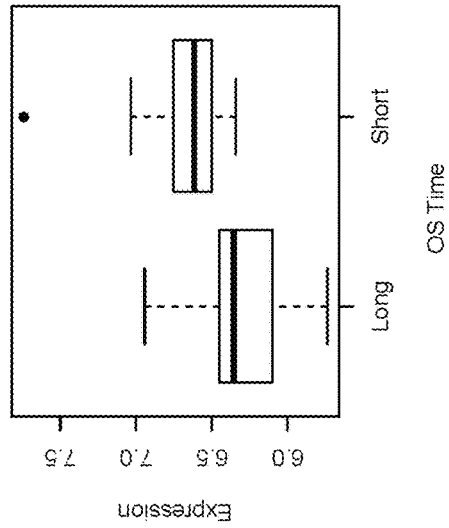
FIG. 9 ERBB2 (pvalue=0.00145)
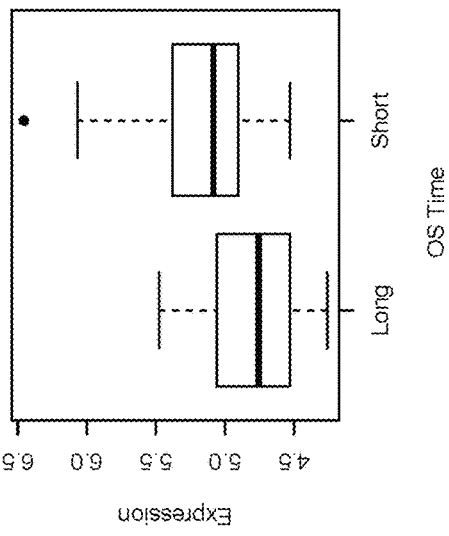
FIG. 11 F3 (pvalue=0.0166)
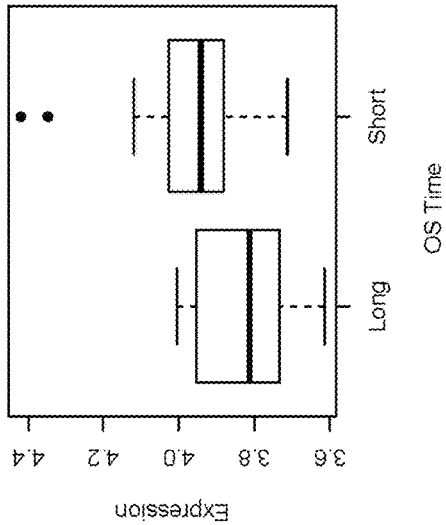
FIG. 10 F2 (pvalue=3.99e-05)
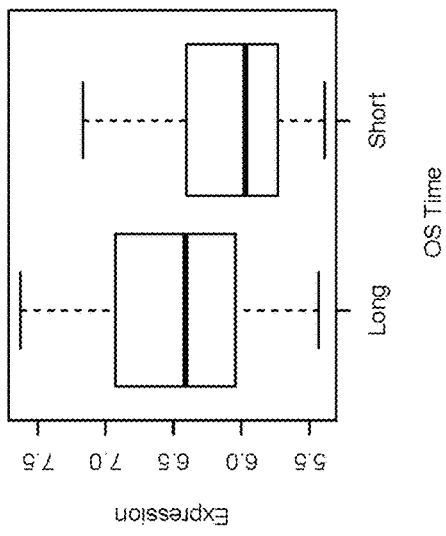
FIG. 12 FLT1 (pvalue=0.000691)

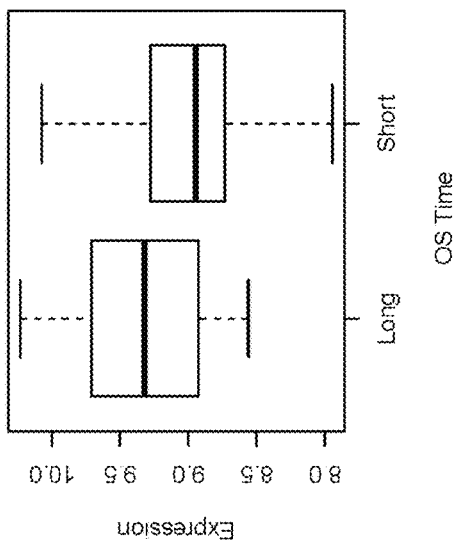
FIG. 13  FOXC2 (pvalue=0.000199)
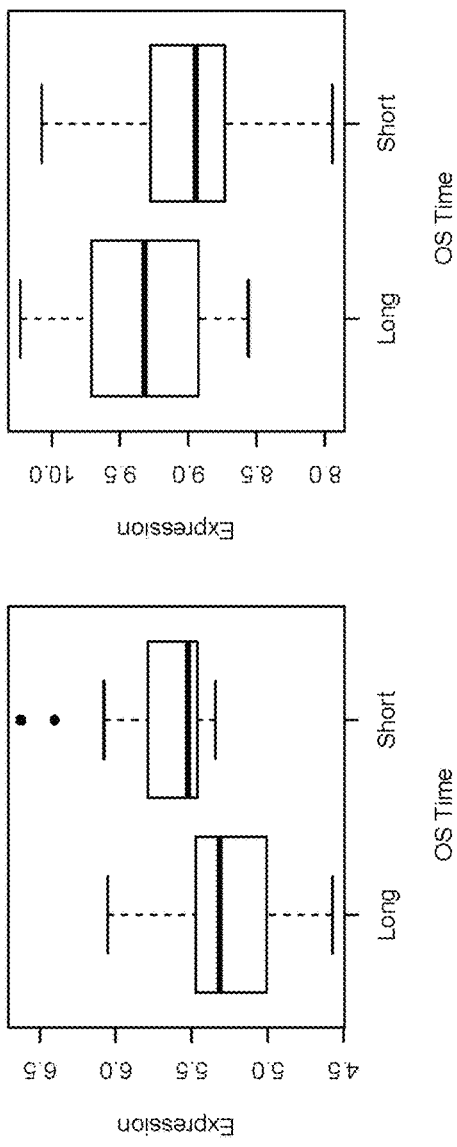
FIG. 14  GUSB (pvalue=0.0495)
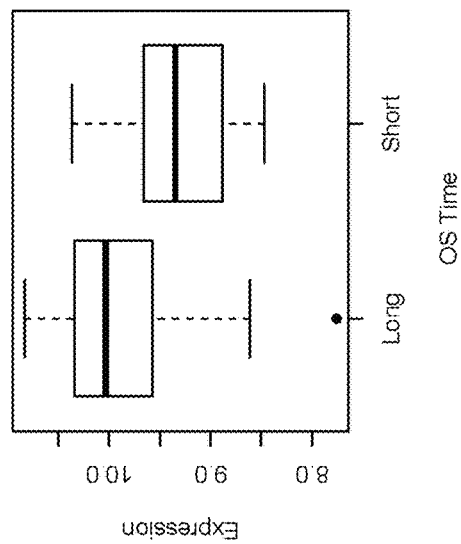
FIG. 15  HGF (pvalue=2.98e−05)
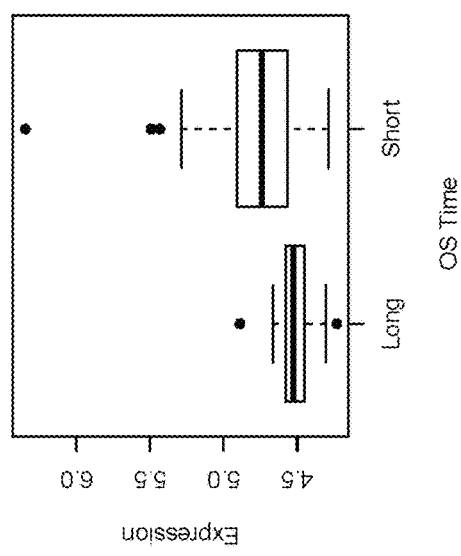
FIG. 16  HIF1A (pvalue=0.000691)

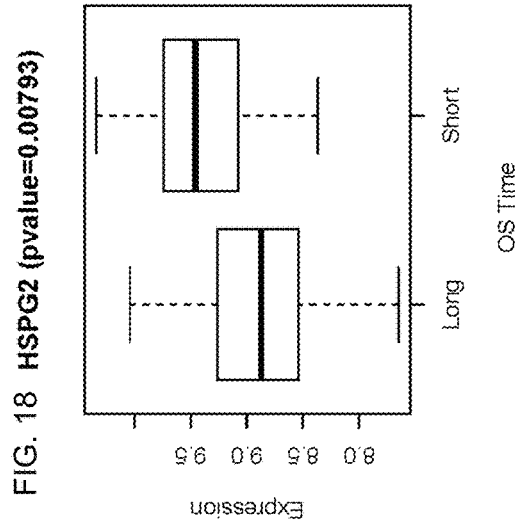
FIG. 17 HPRT1 (pvalue=0.00167)
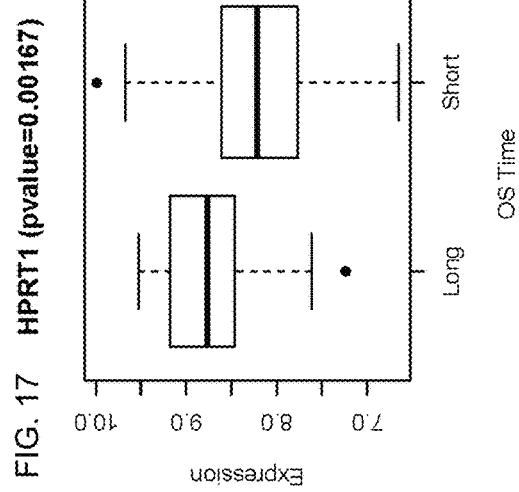
FIG. 18 HSPG2 (pvalue=0.00793)
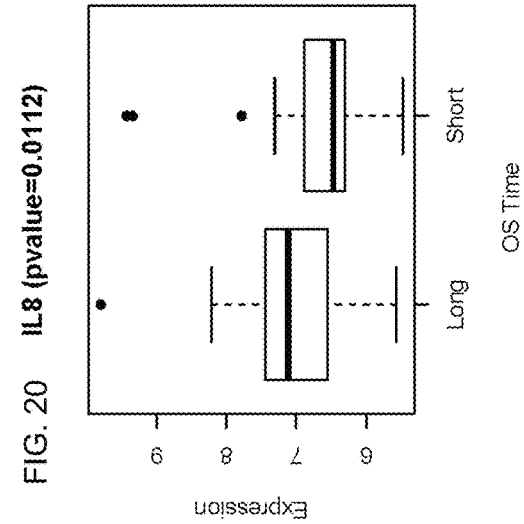
FIG. 19 IL5RA (pvalue=0.0649)
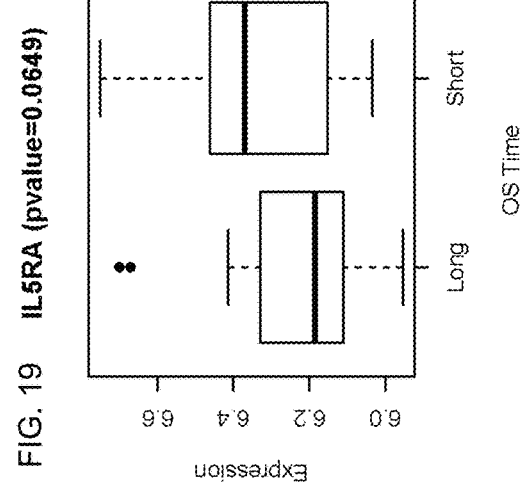
FIG. 20 IL8 (pvalue=0.0112)

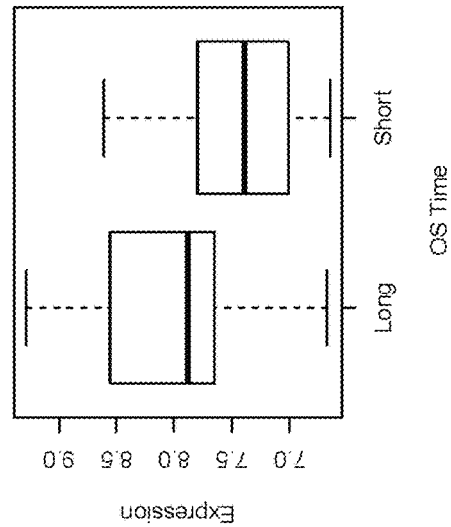
FIG. 21 ITGB3 (pvalue=0.00269)
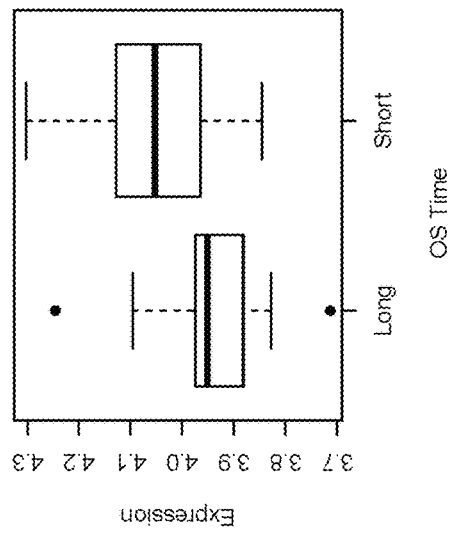
FIG. 22 JAG1 (pvalue=0.000935)
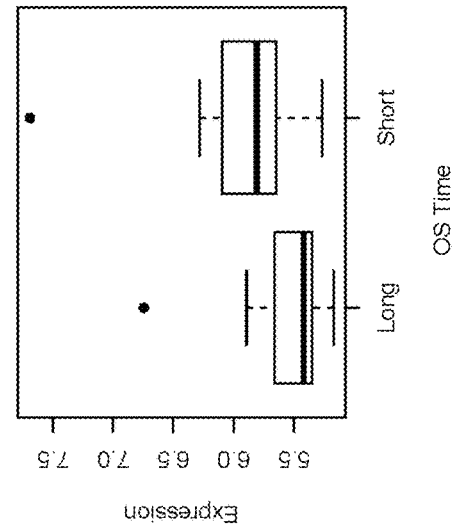
FIG. 23 LECT1 (pvalue=0.0308)
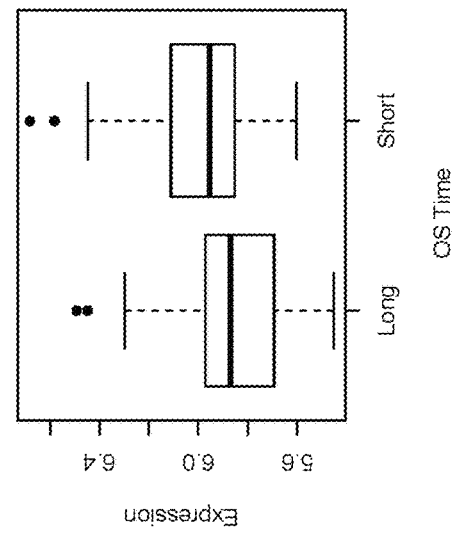
FIG. 24 NOS3 (pvalue=0.000264)

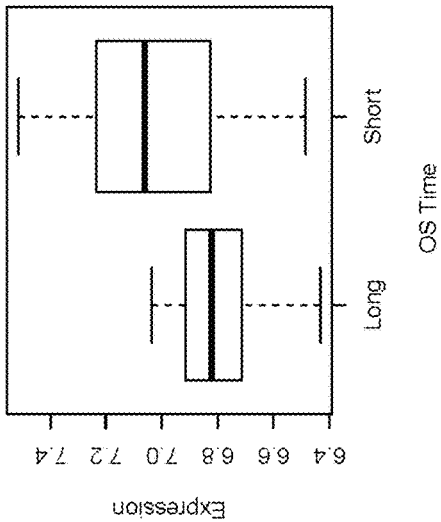
FIG. 25 NRP1 (pvalue=0.00296)
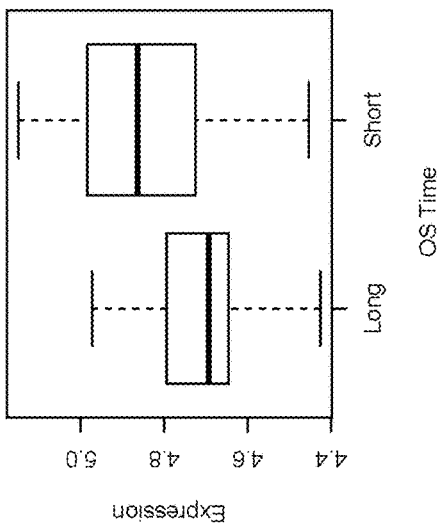
FIG. 26 PF4 (pvalue=0.000746)
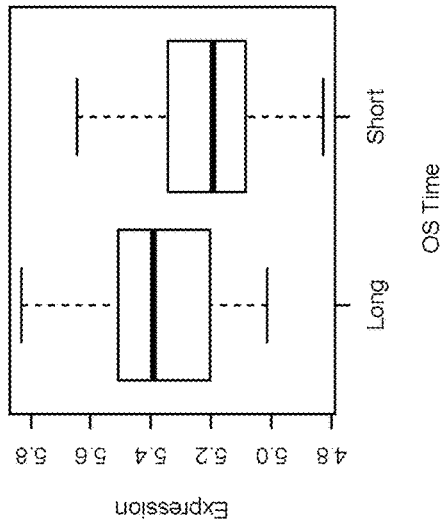
FIG. 27 PLG (pvalue=4.84e-05)
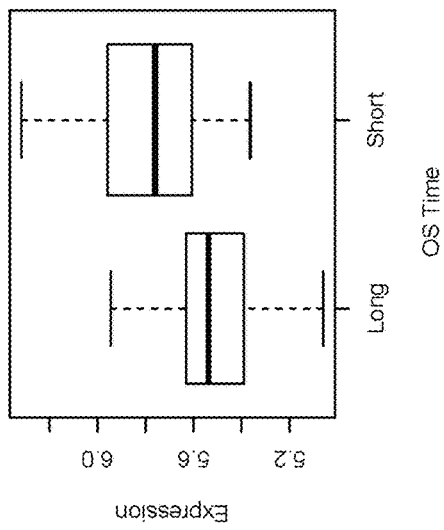
FIG. 28 TEK (pvalue=0.00893)

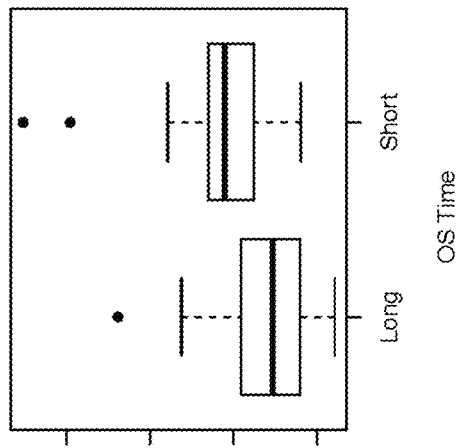
FIG. 29  TGFA (pvalue=0.00135)
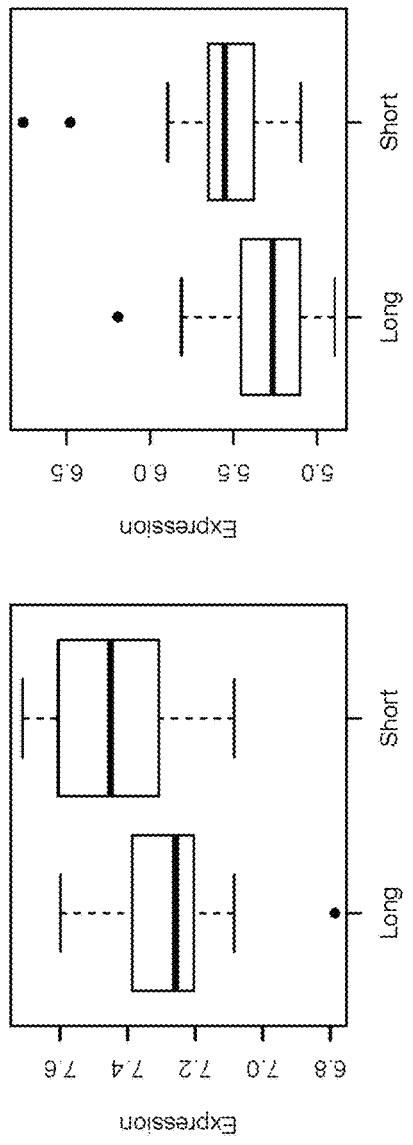
FIG. 30  TNNI1 (pvalue=0.00309)
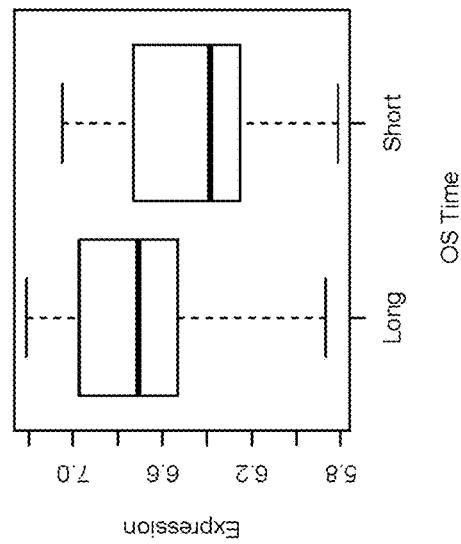
FIG. 31  VASH1 (pvalue=0.00842)

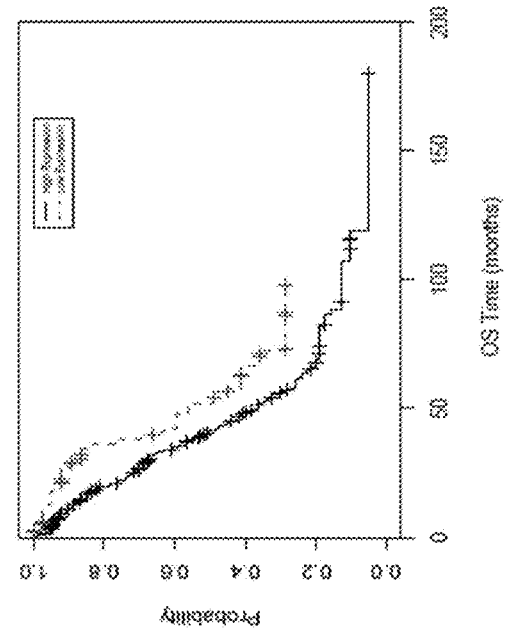
FIG. 34A  FIG. 34B
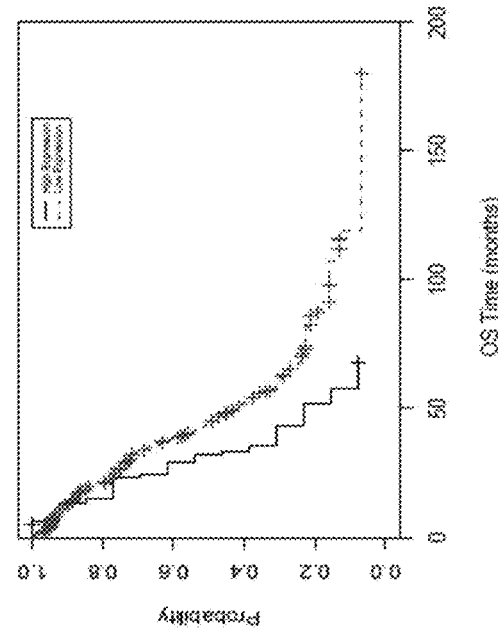
FIG. 35A  FIG. 35B
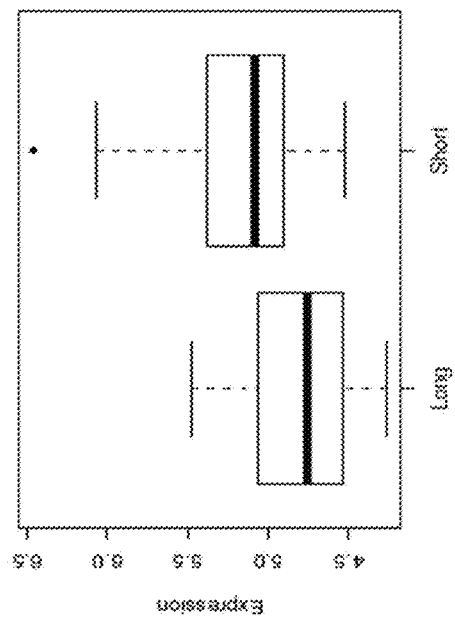
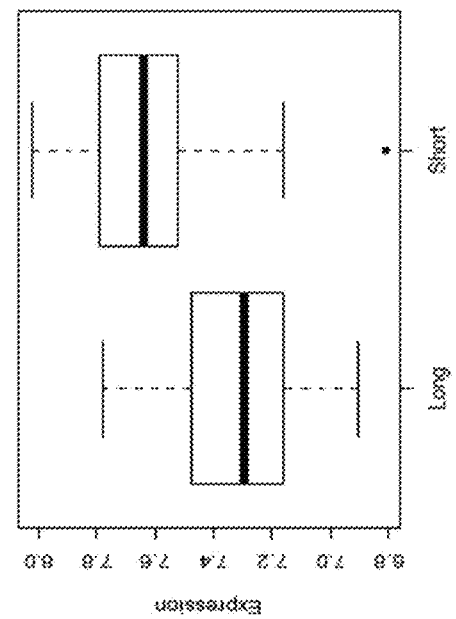

BIOMARKERS OF HIGH-GRADE SEROUS OVARIAN CARCINOMAS

CROSS REFERENCE TO RELATED APPLICATIONS

This application claims the benefit of U.S. provisional patent application No. 61/825,189 filed May 20, 2013 and U.S. provisional patent application No. 61/867,219 filed Aug. 19, 2013, the disclosures of which are hereby incorporated by reference in their entireties.

FEDERAL FUNDING LEGEND

The invention was made with government support under Grant No. 5R25CA126938-03, titled "Integrating Population and Basic Science in cancer Research" awarded by the National Institute of Health/National Cancer Institute. The Government has certain rights in the invention.

TECHNICAL FIELD

The presently disclosed subject matter relates to compositions and methods that enable rationally directed therapies in women with high-grade serous ovarian carcinomas (HGSCs). In particular, the presently disclosed subject matter relates to angiogenic biomarkers and methods and compositions for predicting overall survival (OS) in women with HGSC.

BACKGROUND

Epithelial ovarian cancer (EOC) is considered the most lethal gynecologic malignancy and a leading cause of cancer death in Western industrialized countries including the United States. The majority of ovarian cancer cases are high-grade serous ovarian cancers (HGSCs). Unfortunately, the majority of women are diagnosed with advanced stage disease. Despite surgical advances, novel anti-angiogenic targeted therapies, and improved median survival, few women with HGSCs are cured (Berchuck, Iversen et al. 2009). There is an urgent need to develop innovative and rationally directed therapies to improve outcome in women with this disease.

Many promising biologic agents target tumor angiogenesis, a critical component of solid tumor growth and metastasis (Folkman 1994, Folkman 2002). Angiogenesis has been shown to be an important predictor of tumor behavior in a number of human malignancies and can be measured via microvessel density (MVD) counts. MVD microscopic measurement is an established technique, and known prognostic factor (Weidner, Semple et al. 1991, Weidner, Folkman et al. 1992, Weidner, Carroll et al. 1993, Zatterstrom, Brun et al. 1995, de Jong, van Diest et al. 2000, Hlatky, Hahnfeldt et al. 2002). We and others, previously demonstrated that angiogenesis based on MVD has prognostic significance in EOC. Specifically, women whose ovarian cancers demonstrated higher MVD have a worse survival compared to those with lower counts. (Alvarez, Krigman et al. 1999, Rubatt, Darcy et al. 2009). Furthermore, antiangiogenic therapy with inhibitors of vascular endothelial growth factor (VEGF), a potent proangiogenic factor, has demonstrated anti-tumor activity in women with EOC. (Burger 2007). The antiangiogenic agents studied in EOC include agents such Bevacizumab, an anti vascular endothelial growth factor (VEGF) monoclonal antibody, and multitargeted antiangiogenic tyrosine kinase inhibitors such as BIBF 1120 and Pazopanib. (Teoh and Secord 2012).

The VEGF inhibitor, bevacizumab, has been shown to have activity in ovarian cancer as manifested by a response rate of 20% and a 6-month progression-free survival (PFS) rate of 40% (Burger 2007). Two pivotal phase III trials have demonstrated that bevacizumab combined with chemotherapy followed by maintenance bevacizumab yielded a PFS benefit. In a subset analysis of ICON7, the addition of concurrent and maintenance bevacizumab resulted in improved PFS and overall survival in women with suboptimally debulked stage III disease and stage IV disease. (Perren, Swart et al. 2010, Burger 2011, Teoh and Secord 2012). Despite, initial anti-tumor activity, cancers eventually develop resistance to VEGF-blockade. The mechanism of resistance to VEGF inhibitors has not been completely elucidated. One hypothesis maintains that multiple alternate proangiogenic pathways overcome VEGF inhibition and maintain the proangiogenic tumor environment. (Loges, Schmidt et al. 2010). In order to effectively overcome anti-VEGF resistance, novel alternate targets must be elucidated. Moreover, biomarkers are needed to identify ovarian cancer patients that are most likely to benefit from anti-angiogenic-specific therapy in order to minimize toxicity and cost.

High-grade serous ovarian carcinoma (HGSC) is an aggressive type of epithelial ovarian cancer associated with numerous genetic alterations and poor survival. There remains an urgent unmet need for methods that are predictive of clinical outcome in women with this disease to enable rationally directed therapies to improve outcome in these women. The present disclosure provides such compositions and methods.

SUMMARY

In one embodiment of the present disclosure, a method is provided for determining the overall survival of a subject having high-grade serous ovarian cancer (HGSC), comprising:

quantifying an expression level of one or more biomarkers that are associated with overall survival in ovarian cancer in a biological sample derived from a subject relative to a reference control, wherein the biomarker comprises one or more of EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, TNNI1, AKT1, CD44, F3, GUSB, HIF1A, HPRT1, IL8, JAG1, TEK, and VASH1; and determining one of:

the subject as having a likely shorter overall survival if the expression level of one or more of the biomarkers: EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, and TNNI1 is higher in the biological sample derived from the subject compared to the reference control, or the subject as having a likely longer overall survival if the expression level of one or more of the biomarkers: AKT1, CD44, F3, GUSB, HIF1A, HPRT1, IL8, JAG1, TEK, and VASH1 is higher in the biological sample derived from the subject compared to the reference control.

In one embodiment of the present disclosure, a kit is provided for determining the overall survival of a subject having ovarian cancer, the kit comprising:

primers for quantifying a gene expression level of one or more biomarkers that are associated with overall survival in ovarian cancer in a biological sample derived from a subject relative to a reference control, wherein the primers are for one or more biomarkers comprising EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, TNNI1, AKT1, CD44, F3, GUSB, HIF1A, HPRT1, IL8, JAG1, TEK, and VASH1; and instructions for determining one of:

the subject as having a likely shorter than average overall survival if the expression level of one or more of the biomarkers: EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, and TNNI1 is higher in the biological sample derived from the subject compared to the reference control, or the subject as having a likely longer than average overall survival if the expression level of one or more of the biomarkers: AKT1, CD44, F3, GUSB, HIF1A, HPRT1, IL8, JAG1, TEK, and VASH1 is higher in the biological sample derived from the subject compared to the reference control.

BRIEF DESCRIPTION OF THE DRAWINGS

The foregoing aspects and other features of the invention are explained in the following description, taken in connection with the accompanying drawings.

FIG. 1 is a box graph for biomarker AKT1 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker AKT1 is associated with long OS compared to patients with short OS.

FIG. 2 is a box graph for biomarker ANGPT4 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker ANGPT4 is associated with short OS compared to patients with long OS.

FIG. 3 is a box graph for biomarker ANGPTL3 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker ANGPTL3 is associated with short OS compared to patients with long OS.

FIG. 4 is a box graph for biomarker CD44 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker CD44 is associated with long OS compared to patients with short OS.

FIG. 5 is a box graph for biomarker COL4A3 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker COL4A3 is associated with short OS compared to patients with long OS.

FIG. 6 is a box graph for biomarker CSF3 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker CSF3 is associated with short OS compared to patients with long OS.

FIG. 7 is a box graph for biomarker CUL7 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker CUL7 is associated with short OS compared to patients with long OS.

FIG. 8 is a box graph for biomarker EPHB2 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker EPHB2 is associated with short OS compared to patients with long OS.

FIG. 9 is a box graph for biomarker ERBB2 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker ERBB2 is associated with short OS compared to patients with long OS.

FIG. 10 is a box graph for biomarker F2 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker F2 is associated with short OS compared to patients with long OS.

FIG. 11 is a box graph for biomarker F3 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker F3 is associated with long OS compared to patients with short OS.

FIG. 12 is a box graph for biomarker FLT1 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker FLT1 is associated with short OS compared to patients with long OS.

FIG. 13 is a box graph for biomarker FOXC2 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker FOXC2 is associated with short OS compared to patients with long OS.

FIG. 14 is a box graph for biomarker GUSB showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker GUSB is associated with long OS compared to patients with short OS.

FIG. 15 is a box graph for biomarker HGF showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker HGF is associated with short OS compared to patients with long OS.

FIG. 16 is a box graph for biomarker HIF1A showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker HIF1A is associated with long OS compared to patients with short OS.

FIG. 17 is a box graph for biomarker HPRT1 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker HPRT1 is associated with long OS compared to patients with short OS.

FIG. 18 is a box graph for biomarker HSPG2 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker HSPG2 is associated with short OS compared to patients with long OS.

FIG. 19 is a box graph for biomarker IL5RA showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker IL5RA is associated with a short OS compared to patients with long OS.

FIG. 20 is a box graph for biomarker IL8 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker IL8 is associated with long OS compared to patients with short OS.

FIG. 21 is a box graph for biomarker ITGB3 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker ITGB3 is associated with short OS compared to patients with long OS.

FIG. 22 is a box graph for biomarker JAG1 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker JAG1 is associated with long OS compared to patients with long OS.

FIG. 23 is a box graph for biomarker LECT showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker LECT1 is associated with short OS compared to patients with long OS.

FIG. 24 is a box graph for biomarker NOS3 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker NOS3 is associated with short OS compared to patients with long OS.

FIG. 25 is a box graph for biomarker NRP1 showing that a higher expression level of this biomarker is associated with overall survival (OS) time (either Long: 7 years or more or Short: 3 years or less) in HGSC patients in accordance with one or more embodiments of the present disclosure. Specifically, the graph shows that a higher expression level of the biomarker NRP1 is associated with short OS compared to patients with long OS.

FIG. 26 is a box graph for biomarker PF4 showing that a higher expression level of this biomarker is associated with overall survival (OS) time (either Long: 7 years or more or Short: 3 years or less) in HGSC patients in accordance with one or more embodiments of the present disclosure. Specifically, the graph shows that a higher expression level of the biomarker PF4 is associated with short OS compared to patients with long OS.

FIG. 27 is a box graph for biomarker PLG showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker PLG is associated with short OS compared to patients with long OS.

FIG. 28 is a box graph for biomarker TEK showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker TEK is associated with long OS compared to patients with short OS.

FIG. 29 is a box graph for biomarker TGFA showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker TGFA is associated with short OS compared to patients with long OS.

FIG. 30 is a box graph for biomarker TNNI1 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker TNNI1 is associated with short OS compared to patients with long OS.

FIG. 31 is a box graph for biomarker VASH1 showing that a higher expression level of this biomarker is associated with overall survival (OS) time (either Long: 7 years or more, or Short: 3 years or less) in HGSC patients in accordance with one or more embodiments of the present disclosure. Specifically, the graph shows that a higher expression level of the biomarker VASH1 is associated with long OS compared to patients with short.

FIGS. 34A-34B are graphs for biomarker ERBB2 showing an association between increased gene expression levels of the biomarker and overall survival (OS) time in accordance with one or more embodiments of the present disclosure. A) A box graph of data collected from a study conducted at Duke University showing that a higher expression level of the biomarker ERBB2 is associated with a decrease in OS of 3 years or less. B) A graph of probability versus OS time for high expression (solid line) and low expression (dashed line) of the biomarker ERBB2 using data from the publically available database "The Cancer Genome Atlas" (TCGA) confirming the direction of the association shown in (A) which is higher expression levels of ERBB2 associated with shorter OS.

FIGS. 35A-35B are graphs for biomarker EPHB2 showing an association between increased gene expression levels of the biomarker and overall survival (OS) time in accordance with one or more embodiments of the present disclosure. A) A box graph of data collected from a study conducted at Duke University showing that a higher expression level of the biomarker EPHB2 is associated with a decrease in OS of 3 years or less. B) A graph of probability versus OS time for high expression (solid line) and low expression (dashed line) of the biomarker EPHB2 using data from the publically available database "The Cancer Genome Atlas" (TCGA) confirming the direction of the association shown in (A) which is higher expression levels of EPHB2 associated with shorter OS.

DETAILED DESCRIPTION

Figures 32A, 32B:
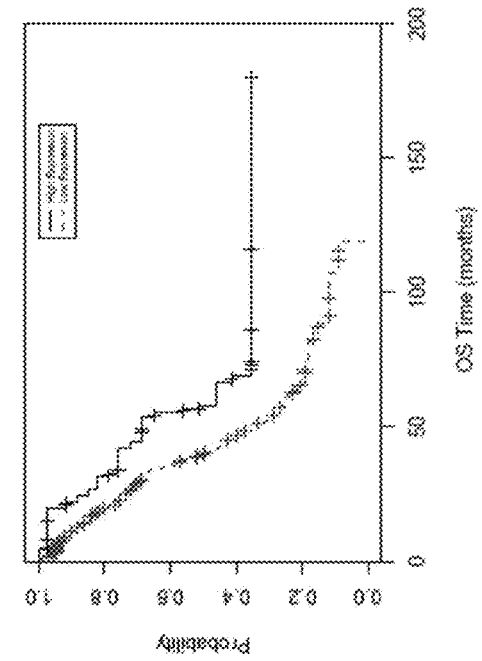
FIGS. 32A-32B are graphs for biomarker AKT1 showing an association between increased gene expression levels of the biomarker and overall survival (OS) time in accordance with one or more embodiments of the present disclosure. A) A box graph of data collected from a study conducted at Duke University showing that a higher expression level of the biomarker AKT1 is associated with an increase in OS of 7 years or more. B) A graph of probability versus OS time for high expression (solid line) and low expression (dashed line) of the biomarker AKT1 using data from the publically available database "The Cancer Genome Atlas" (TCGA) confirming the direction of the association shown in (A) which is higher expression levels of AKT1 associated with longer OS.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The present disclosure describes, in one aspect, investigation of the association between angiogenic gene expression profiles and overall survival (OS) in women with high-grade serous ovarian carcinomas (HGSCs). The results improve the understanding of tumor angiogenesis regulation and establish quantifiable and reproducible angiogenic biomarkers to direct therapy in women with HGSC.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

As used herein, the term "biomarker" refers to a naturally occurring biological molecule present in a subject at varying concentrations useful in predicting the risk or incidence of a disease, the aggressiveness of a disease or a condition, or the likelihood of surviving a disease or condition, such as ovarian cancer. For example, the biomarker can be a nucleic acid or a protein present in higher or lower amounts in a subject as compared to a control that indicates the aggressiveness of a disease/condition or likelihood of survival of said disease/condition. The biomarker can include nucleic acids, ribonucleic acids, proteins, phosphopeptides, etc. and combinations thereof used as an indicator or marker for ovarian cancer aggressiveness and/or survivability in a subject.

As used herein, the term "ovarian cancer" refers to those types of cancers that originate in tissues of the ovary (one of a pair of female reproductive glands in which the ova, or eggs, are formed). Most ovarian cancers are either ovarian epithelial carcinomas (cancer that begins in the cells on the surface of the ovary) or malignant germ cell tumors (cancer that begins in egg cells).

"About" is used to provide flexibility to a numerical range endpoint by providing that a given value may be "slightly above" or "slightly below" the endpoint without affecting the desired result.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. For example, such therapies may include surgery, medications (hormonal therapy and/or chemotherapy), radiation, immunotherapy and the like. Such treatments are well known and particular to the patient and can be readily determined by one skilled in the art The term "effective amount" or "therapeutically effective amount" refers to an amount sufficient to effect beneficial or desirable biological and/or clinical results.

In some embodiments, the biomarker for ovarian cancer is selected from the group consisting of 31 biomarker genes as shown in Table 1 below and combinations thereof. In the study described herein in the Examples, 43 features linked to the 31 angiogenic genes shown in Table 1 were determined to be significantly associated with longer overall survival (OS) (FDR q-value (q)<0.05) in high grade serous carcinoma in an adjusted microarray result analysis. The association of these biomarkers with OS is shown in FIGS. 1-31. In addition, the direction of the association of biomarker expression with OS was confirmed using data from each of the external databases "The Cancer Genome Atlas" (TCGA) and the "Genomic Spatial Event" (GSE; databases GSE26712 and GSE 14764) for a subset of the 31 biomarker genes and these data are shown in FIGS. 32-40.

A higher expression level of the biomarkers EPHB2, ERBB2, FLT1, PF4, NRP1, COL4A3, ANGPTL3, ANGPT4, CSF3, CUL7, F2, FOXC2, HGF, HSPG2, IL5RA, ITGB3, LECT1, NOS3, NRP1, PLG, TGFA, and TNNI1 are associated with a likely shorter OS and a higher expression level of the biomarkers AKT1, CD44, F3, GUSB, HIF1A, HPRT1, IL8, JAG1, TEK, and VASH1 are associated with a likely longer OS. The externally confirmed subset includes biomarker genes: AKT1 (q=0.018), CD44 (q<0.003), EPHB2 (q<0.009), ERBB2 (q<0.019), FLT1 (q=0.03); PF4 (q=0.02), NRP1 (q=0.02), COL4A3 (q<0.019), and ANGPTL3 (q=0.02). Increased gene expression of AKT1 and CD44 was associated with longer survival. In contrast, high expression of EPHB2, ERBB2, FLT1; PF4, NRP1, COL4A3, and ANGPTL3 was associated with shorter survival.

TABLE 1

Thirty one angiogenic biomarker genes for overall survival (OS) in high grade serous ovarian carcinoma (HGSC).

| Gene symbol | Probe ID | OS p-value | OS q-value | HR | Long OS Associated with |
|---|---|---|---|---|---|
| *AKT1 | 207163_s_at | 0.002 | 0.02 | 0.44 | HE |
| ANGPT4 | 221134_at | 0.004 | 0.02 | 5.75 | LE |
| **ANGPTL3 | 219803_at | 0.002 | 0.02 | 6.45 | LE |
| *CD44 | 212063_at | 0.00002 | 0.002 | 0.48 | HE |
| **COL4A3 | 216896_at | 0.010 | 0.04 | 11.3 | LE |
| CSF3 | 207442_at | 0.007 | 0.03 | 4.86 | LE |
| CUL7 | 36084_at | 0.00008 | 0.01 | 5.35 | LE |
| *EPHB2 | 210651_s_at | 0.0004 | 0.01 | 8.12 | LE |
| *ERBB2 | 210930_s_at | 0.00 | 0.02 | 2.86 | LE |
| F2 | 205754_at | 0.01 | 0.04 | 2.74 | LE |
| F3 | 204363_at | 0.00 | 0.02 | 0.41 | HE |
| **FLT1 | 210287_s_at | 0.01 | 0.03 | 20.73 | LE |
| FOXC2 | 214520_at | 0.01 | 0.03 | 2.58 | LE |
| GUSB | 202605_at | 0.01 | 0.05 | 0.49 | HE |
| HGF | 210998_s_at | 0.0002 | 0.01 | 2.72 | LE |
| HIF1A | 200989_at | 0.01 | 0.03 | 0.68 | HE |
| HPRT1 | 202854_at | 0.0001 | 0.01 | 0.48 | HE |
| HSPG2 | 201655_s_at | 0.001 | 0.02 | 2.46 | LE |
| IL5RA | 210744_s_at | 0.011 | 0.04 | 6.82 | LE |
| IL8 | 202859_x_at | 0.001 | 0.02 | 0.62 | HE |
| ITGB3 | 211579_at | 0.003 | 0.02 | 23.36 | LE |
| JAG1 | 209099_x_at | 0.001 | 0.02 | 0.48 | HE |
| LECT1 | 206309_at | 0.008 | 0.04 | 2.89 | LE |
| NOS3 | 205581_s_at | 0.0002 | 0.01 | 1.97 | LE |
| **NRP1 | 210615_at | 0.003 | 0.02 | 14.77 | LE |
| **PF4 | 206390_x_at | 0.003 | 0.02 | 10.17 | LE |
| PLG | 209977_at | 0.002 | 0.02 | 7.17 | LE |
| TEK | 206702_at | 0.015 | 0.049 | 0.14 | HE |
| TGFA | 211258_s_at | 0.001 | 0.02 | 19.2 | LE |
| TNNI1 | 205177_at | 0.014 | 0.05 | 2.04 | LE |
| VASH1 | 203940_s_at | 0.010 | 0.04 | 0.38 | HE |

HE = High Expression; LE = Low Expression; HR = Hazard Ratio; q-value = adjusted p-value
*Genes that were confirmed in the public TCGA data base.
**Genes that were confirmed in the public data bases GSE26712 and GSE 14764.

The data provided herein demonstrate associations between overall survival and differential expression of a novel panel of 31 biomarker genes associated with angiogenesis. The biomarkers include members of the ANG-TIE-TEK pathway. In addition, these data include the first report that overexpression of an ANG-like gene (ANGPTL3) is associated with decreased overall survival in HGSC.

The 31 biomarker genes shown in Table 1 were further analyzed for an association with TP53(P53) mutation status. The results indicated that there is a significant association between gene expression levels in a subset of the 31 angiogenic related genes and overall survival (OS). Specifically, 8 of the biomarker genes had significant association with P53 mutation status (p-value ≤0.05) and the data are shown in FIGS. 41-48 and Table 2 below. Biomarker genes CUL7, FLT1, PLG, and CD44 had a significant association with P53 mutation status. A higher expression level of CUL7, FLT1, and PLG was associated with shorter overall survival, in addition to these biomarker genes also showing a significant association with P53 mutation status, which status can be a separate indicator of tumor aggressiveness.

TABLE 2

Genes that were associated with OS and TP53(P53) mutation status:

| Affymetrix Probe ID | Gene symbol | Outcome mutation | p-value | High RNA expression of the gene associated with |
|---|---|---|---|---|
| 200989_at | HIF1A | P53 | 0.005 | more P53 wild type |
| 210930_s_at | ERBB2 | P53 | 0.013 | more P53 wild type |
| 210287_s_at | FLT1 | P53 | 0.019 | more P53 mutation |
| 210651_s_at | EPHB2 | P53 | 0.022 | more P53 wild type |
| 203558_at | CUL7 | P53 | 0.036 | more P53 mutation |
| 214520_at | FOXC2 | P53 | 0.045 | more P53 wild type |
| 209977_at | PLG | P53 | 0.05 | more P53 mutation |
| 212063_at | CD44 | P53 | 0.056 | more P53 mutation |

The present disclosure provides biomarkers useful for determining the aggressiveness of ovarian cancer in a subject and/or the likelihood of survival for a subject suffering from ovarian cancer. Advantageously, the methods of the present disclosure are noninvasive, highly specific, and sensitive.

In one embodiment, the present disclosure profiles biomarkers found in biological samples (e.g., tissues, cells, tumor tissue, biopsies and the like) for determining the aggressiveness of an ovarian cancer in a subject and/or the likelihood of survival for a subject suffering from ovarian cancer.

In one embodiment, the present disclosure identifies gene expression profiles as biomarkers for determining the aggressiveness of an ovarian cancer in a subject and/or the likelihood of survival for a subject suffering from ovarian cancer. The inventors have determined that certain biomarkers are directly involved in ovarian cancer aggressiveness and/or likelihood of survival, and their expression pattern in a biological sample can be associated with the pathophysiological status of the subject suffering from ovarian cancer.

One aspect of the present disclosure provides biomarkers useful for determining the aggressiveness of an ovarian cancer in a subject In one embodiment, the present disclosure provides biomarkers that are differentially expressed, such as upregulated, down-regulated, or disregulated in a condition such as ovarian cancer, as compared to normal populations who do not have the condition, such as ovarian cancer.

In one embodiment of the present disclosure, a method is provided for determining the overall survival of a subject having high-grade serous ovarian cancer (HGSC), comprising: quantifying an expression level of one or more biomarkers that are associated with overall survival in ovarian cancer in a biological sample derived from a subject relative to a reference control, wherein the biomarker comprises one or more of EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, TNNI1, AKT1, CD44, F3, GUSB, HIF1A, HPRT1, IL8, JAG1, TEK, and VASH1; and determining one of: the subject as having a likely shorter overall survival if the expression level of one or more of the biomarkers: EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, and TNNI1 is higher in the biological sample derived from the subject compared to the reference control or the subject as having a likely longer overall survival if the expression level of one or more of the biomarkers: AKT1, CD44, F3, GUSB, HIF1A, HPRT1, IL8, JAG1, TEK, and VASH1 is higher in the biological sample derived from the subject compared to the reference control. In the method, the biomarkers can consist of one or more of EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, TNNI1, AKT1, CD44, F3, GUSB, HIF1A, HPRT1, IL8, JAG1, TEK, and VASH1.

In the method for determining the OS of a subject having HGSC, the likely shorter overall survival can be 3 years or less and the likely longer overall survival can be 7 years or more.

In the method for determining the OS of a subject having HGSC, the method can further comprise administering appropriate ovarian cancer therapy to the subject based on the determination of overall survival.

In the method for determining the OS of a subject having HGSC, the expression level can be gene expression level and the quantifying can be carried out by one or a combination of Polymerase Chain Reaction, Real Time-Polymerase Chain Reaction, Real Time Reverse Transcriptase-Polymerase Chain Reaction, Northern blot analysis, in situ hybridization, and probe array.

In the method for determining the OS of a subject having HGSC, the biological sample can comprise one or a combination of tumor tissue, tumor cells, or biopsy tissue.

In the method for determining the OS of a subject having HGSC, the subject can be a mammal. In the method, the subject can be a human.

In the method for determining the OS of a subject having HGSC, the biomarkers can comprise one or more of EPHB2, ERBB2, FLT1, PF4, NRP1, COL4A3, ANGPTL3, AKT1, and CD44. In the method, the biomarkers can consist of one or more of EPHB2, ERBB2, FLT1, PF4, NRP1, COL4A3, ANGPTL3, AKT1, and CD44.

In the method for determining the OS of a subject having HGSC, the biomarker can comprise ANGPTL3. In the method, the biomarker can consist of ANGPTL3.

In the method for determining the OS of a subject having HGSC, the biomarkers can comprise one or more of CUL7, FLT1, and PLG. In the method, the biomarkers can consist of one or more of CUL7, FLT1, and PLG.

In one embodiment of the present disclosure, a kit is provided for determining the overall survival of a subject having ovarian cancer, the kit comprising: primers for quantifying a gene expression level of one or more biomarkers that are associated with overall survival in ovarian cancer in a biological sample derived from a subject relative to a reference control, wherein the primers are for one or more biomarkers comprising EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, TNNI1, AKT1, CD44, F3, GUSB, HIF1A, HPRT1, IL8, JAG1, TEK, and VASH1; and instructions for determining one of: the subject as having a likely shorter than average overall survival if the expression level of one or more of the biomarkers: EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, and TNNI1 is higher in the biological sample derived from the subject compared to the reference control or the subject as having a likely longer than average overall survival if the expression level of one or more of the biomarkers: AKT1, CD44, F3, GUSB, HIF1A, HPRT1, IL8, JAG1, TEK, and VASH1 is higher in the biological sample derived from the subject compared to the reference control. In the kit, the one or more biomarkers can consist of EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, TNNI1, AKT1, CD44, F3, GUSB, HIF1A, HPRT1, IL8, JAG1, TEK, and VASH1.

In the kit for determining the overall survival of a subject having high-grade serous ovarian cancer (HGSC), the likely shorter overall survival can be 3 years or less and the likely longer overall survival can be 7 years or more.

The kit for determining the overall survival of a subject having HGSC can further comprise one or more hybridization probes specific for the biomarker(s). The kit can further comprise a solid support having the one or more hybridization probes attached thereto.

In the kit for determining the overall survival of a subject having HGSC, the biological sample can comprise tumor tissue, tumor cells, or biopsy tissue.

In the kit for determining the overall survival of a subject having HGSC, the subject can be a mammal. In the kit, the subject can be a human.

In the kit for determining the overall survival of a subject having HGSC, the biomarkers can consist of one or more of EPHB2, ERBB2, FLT1, PF4, NRP1, COL4A3, ANGPTL3, AKT1, and CD44. In the kit, the biomarkers can comprise one or more of EPHB2, ERBB2, FLT1, PF4, NRP1, COL4A3, ANGPTL3, AKT1, and CD44.

In the kit for determining the overall survival of a subject having HGSC, the biomarker can comprise ANGPTL3. In the kit, the biomarker can consist of ANGPTL3.

In the kit for determining the overall survival of a subject having HGSC, the biomarkers can comprise one or more of CUL7, FLT1, and PLG. In the kit, the biomarkers can consist of CUL7, FLT1, and PLG.

In some embodiments, the biomarker comprises a protein. In one embodiment, the biomarker(s) associated with non- or less-aggressive ovarian cancer comprise, consist of, or consist essentially of one or more of the following proteins: AKT1, CD44 and/or TEK and combinations thereof.

In another embodiment, the biomarker(s) associated with aggressive ovarian cancer may comprise, consist of, of consist essentially of the protein EPHB2, ERBB2/HER2, PF4, ANGPT4, ANGPTL3, NOS3, HGF, HSPG2, IL5RA, GUSB, F2, CUL7 and/or LECT1.

In another embodiment, the biomarker(s) associated with likelihood of survival from ovarian cancer may comprise, consist of, or consist essentially of one or more of the following proteins: AKT1, CD44 and/or TEK and combinations thereof. Biomarker(s) associated with a decreased likelihood of survival from ovarian cancer may comprise, consist of, or consist essentially of one or more of the following proteins: EPHB2, ERBB2/HER2, PF4, ANGPT4, ANGPTL3, NOS3, HGF, HSPG2, IL5RA, GUSB, F2, CUL7 and LECT1.

In one embodiment, the present disclosure provides a method for determining the aggressiveness of an ovarian cancer in a subject comprising, consisting of, or consisting essentially of: (a) determining a biomarker expression profile (expression level) in a biological sample from the subject; (b) characterizing the subject's biomarker profile; (c) comparing the subject's biomarker profile with the biomarker profile of a control from subjects not at risk of ovarian cancer; and (d) administering an appropriate ovarian cancer therapy if one or more of the biomarkers are expressed.

In another embodiment, the present disclosure provides a method for determining the likelihood of survival of a subject suffering from ovarian cancer comprising, consisting of, or consisting essentially of: (a) determining a biomarker expression profile (expression level) in a biological sample from the subject; (b) characterizing the subject's biomarker profile; (c) comparing the subject's biomarker profile with the biomarker profile of a control profile from subjects not at risk of ovarian cancer; and (d) administering an appropriate ovarian cancer therapy if one or more of the biomarkers are expressed.

In one embodiment, the method further includes obtaining the biological sample from the subject. In one embodiment, the determination of the aggressiveness of an ovarian cancer and/or the likelihood of survival of a person suffering from ovarian cancer can be determined by comparing the subjects biomarker profile to a reference biomarker profile, such as one that corresponds to biological samples obtained from a normal population that do not have a condition such as ovarian cancer, or that corresponds to biological samples obtained from a population that have a condition such as ovarian cancer. Optionally, the reference profile comprises multiple biomarker expression profiles, with each corresponding to a different stage of a condition such as ovarian cancer.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that is at for, or suffering from, ovarian cancer.

The term "biological sample" as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, mucus and tears. In one embodiment, the biological sample is a blood sample (such as a plasma sample) or biopsy sample (such as a tissue/cell sample). A biological sample may be obtained directly from a subject (e.g., by blood or tissue sampling) or from a third party (e.g., received from an intermediary, such as a healthcare provider or lab technician).

One aspect of the present disclosure provides a method of determining the aggressiveness of an ovarian cancer in a subject comprising quantifying the amount of at least one biomarker present in a biological sample derived from the subject, wherein the biomarker is associated with ovarian cancer aggressiveness. In certain embodiments, the overexpression of AKT1, TEK and/or CD44 are indicative of a less aggressive ovarian cancer. In other embodiments, the overexpression of one or more of the following proteins: EPHB2, ERBB2/HER2, PF4, ANGPT4, ANGPTL3, NOS3, HGF, HSPG2, IL5RA, GUSB, F2, CUL7 and LECT is indicative of a more aggressive ovarian cancer.

Another aspect of the present disclosure provides a method of predicting the likely survival rate of a subject suffering from ovarian cancer comprising quantifying the amount of at least one biomarker present in a biological sample derived from the subject, wherein the biomarker is associated with patient survival. In certain embodiments, an increased presence of CD44, AKT1, and/or TEK are indicative of a greater chance of survival. In other certain embodiments, an increased expression of EPHB2, ERBB2/HER2, PF4, ANGPT4, ANGPTL3, NOS3, HGF, HSPG2, IL5RA, GUSB, F2, CUL7 and/or LECT are indicative of a less chance of survival.

Another aspect of the present disclosure provides a method of determining the aggressiveness of an ovarian cancer in a subject comprising: (a) obtaining a biological sample from a subject; (b) determining the expression level of one or more biomarkers that are associated with ovarian cancer aggressiveness in the biological sample; (c) comparing the expression level of the biomarkers in the biological sample with that of a control, wherein the presence of one or more of the biomarkers in the sample that is in an amount greater than that of the control indicates the ovarian cancer is not aggressive; and (d) administering appropriate ovarian cancer therapy if one or more of the biomarkers are expressed. In certain embodiments, the presence of AKT1, TEK and/or CD44 in an amount greater than that of a control are indicative of a less aggressive ovarian cancer.

Another aspect of the present disclosure provides a method of determining the aggressiveness of an ovarian cancer of a subject comprising: (a) obtaining a biological sample from a subject; (b) determining the expression level of one or more biomarkers that are associated with ovarian cancer aggressiveness in the biological sample; (c) comparing the expression level of the biomarkers in the biological sample with that of a control, wherein the presence of one or more of the biomarkers in the sample that is in an amount greater than that of the control indicates the ovarian cancer is aggressive; and (d) administering an appropriate ovarian cancer therapy if one or more of the biomarkers are expressed. In other embodiments, the presence of EPHB2, ERBB2/HER2, PF4, ANGPT4, ANGPTL3, NOS3, HGF, HSPG2, IL5RA, GUSB, F2, CUL7 and/or LECT in an amount greater than that of a control is indicative of a more aggressive ovarian cancer.

Another aspect of the present disclosure provides a composition of matter comprising, consisting of, or consisting essentially of: (a) a probe array for determining a biomarker level in a sample, the array comprising of a plurality of probes that hybridizes to one or more biomarkers that are associated with ovarian cancer aggressiveness and/or likelihood of survival; or (b) a kit for determining a biomarker level in a sample, comprising the probe array of (a) and instructions for carrying out the determination of biomarker expression level in the sample. In certain embodiments the probe array of (a) further comprises a solid support with the plurality of probes attached thereto.

The present disclosure provides a method of determining ovarian cancer aggressiveness and/or likelihood of survival of a subject suffering from ovarian cancer on at least one sample obtained from an individual. The individual may be any mammal, but is preferably a human. The present disclosure may involve obtaining more than one sample, such as two samples, such as three samples, four samples or more from individuals, and preferably the same individual. This allows the relative comparison of the level of expression between the two samples. Alternatively, a single sample may be compared against a "standardized" sample, such a sample comprising material or data from several samples, preferably also from several individuals.

Before analyzing the sample, it will often be desirable to perform one or more sample preparation operations upon the sample. Typically, these sample preparation operations will include such manipulations as concentration, suspension, extraction of intracellular material, e.g., proteins/phosphopeptides from tissue/whole cell samples and the like.

Any method required for the processing of a sample prior to detection by any of the methods noted herein falls within the scope of the present disclosure. These methods are typically well known by a person skilled in the art.

It is within the general scope of the present disclosure to provide methods for the detection of protein biomarker. An aspect of the present disclosure relates to the detection of the proteins as described in the plots and graphs of the figures contained herein. As used herein, the term "detect" or "determine the presence of" refers to the qualitative measurement of undetectable, low, normal, or high concentrations of one or more biomarkers such as, for example, nucleic acids, ribonucleic acids, or polypeptides, proteins, phosphopeptides and other biological molecules. Detection may include 1) detection in the sense of presence versus absence of one or more biomarkers as well as 2) the registration/quantification of the level or degree of expression of one or more biomarkers, depending on the method of detection employed. The term "quantify" or "quantification" may be used interchangeable, and refer to a process of determining the quantity or abundance of a substance in a sample (e.g., a biomarker), whether relative or absolute. For example, quantification may be determined by methods including but not limited to, micro-array analysis, qRT-PCR, band intensity on a Northern or Western blot, or by various other methods known in the art.

The detection of one or more biomarker molecules allows for the determination of ovarian cancer aggressiveness and/or likelihood of survival. The classification of such conditions is of relevance both medically and scientifically and may provide important information useful for the diagnosis, prognosis and treatment of the condition.

Any method of detection falls within the general scope of the present disclosure. The detection methods may be generic for the detection of proteins, phosphopeptides, nucleic acids, polypeptides and the like. The detection methods may be directed towards the scoring of a presence or absence of one or more biomarker molecules or may be useful in the detection of expression levels.

The detection methods can be divided into two categories herein referred to as in situ methods or screening methods. The term in situ method refers to the detection of protein, phosphopeptide, and/or nucleic acid molecules in a sample wherein the structure of the sample has been preserved. This may thus be a biopsy (e.g., a tissue biopsy) wherein the structure of the tissue is preserved. In situ methods are generally histological i.e. microscopic in nature and include but are not limited to methods such as: in situ hybridization techniques and in situ PCR methods.

Screening methods generally employ techniques of molecular biology and most often require the preparation of the sample material in order to access the nucleic acid and/or polypeptide molecules to be detected. Screening methods include, but are not limited to methods such as: Array systems, affinity matrices, Northern blotting and PCR techniques, such as real-time quantitative RT-PCR.

One aspect of the present disclosure is to provide a probe which can be used for the detection of a protein, phosphopeptide, nucleic acid and/or polypeptide molecule as defined herein. A probe as defined herein is a specific sequence of a nucleic acid and/or polypeptide used to detect nucleic acids and/or polypeptides by hybridization. For example, a nucleic acid is also here any nucleic acid, natural or synthetic such as DNA, RNA, LNA or PNA. A probe may be labeled, tagged or immobilized or otherwise modified according to the requirements of the detection method chosen. A label or a tag is an entity making it possible to identify a compound to which it is associated. It is within the scope of the present disclosure to employ probes that are labeled or tagged by any means known in the art such as but not limited to: radioactive labeling, fluorescent labeling and enzymatic labeling. Furthermore the probe, labeled or not, may be immobilized to facilitate detection according to the detection method of choice and this may be accomplished according to the preferred method of the particular detection method.

Another aspect of the present disclosure regards the detection of nucleic acid and/or polypeptide molecules by any method known in the art. In the following are given examples of various detection methods that can be employed for this purpose, and the present disclosure includes all the mentioned methods, but is not limited to any of these.

In situ hybridization (ISH) applies and extrapolates the technology of nucleic acid and/or polypeptide hybridization to the single cell level, and, in combination with the art of cytochemistry, immunocytochemistry and immunohistochemistry, permits the maintenance of morphology and the identification of cellular markers to be maintained and identified, allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). DNA ISH can be used to determine the structure of chromosomes and the localization of individual genes and optionally their copy numbers. Fluorescent DNA ISH (FISH) can for example be used in medical diagnostics to assess chromosomal integrity. RNA ISH is used to assay expression and gene expression patterns in a tissue/across cells, such as the expression of miRNAs/nucleic acid molecules. Sample cells are treated to increase their permeability to allow the probe to enter the cells, the probe is added to the treated cells, allowed to hybridize at pertinent temperature, and then excess probe is washed away. A complementary probe is labeled with a radioactive, fluorescent or antigenic tag, so that the probe's location and quantity in the tissue can be determined using autoradiography, fluorescence microscopy or immunoassay, respectively. The sample may be any sample as herein described. The probe is likewise a probe according to any probe based upon the biomarkers mentioned herein.

An aspect of the present disclosure includes the method of detection by in situ hybridization as described herein.

In situ PCR is the PCR based amplification of the target nucleic acid sequences prior to ISH. For detection of RNA, an intracellular reverse transcription (RT) step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR the cells are cytocentrifugated onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens. Detection of intracellular PCR-products is achieved by one of two entirely different techniques. In indirect in situ PCR by ISH with PCR-product specific probes, or in direct in situ PCR without ISH through direct detection of labeled nucleotides (e.g. digoxigenin-11-dUTP, fluorescein-dUTP, $^3$H-CTP or biotin-16-dUTP) which have been incorporated into the PCR products during thermal cycling.

An embodiment of the present disclosure concerns the method of in situ PCR as mentioned herein above for the detection of nucleic acid molecules as detailed herein.

A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used e.g. to measure the expression levels of large numbers of polypeptides/proteins/nucleic acids simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

An aspect of the present disclosure regards the use of microarrays for the expression profiling of biomarkers in conditions such as ovarian cancer aggressiveness and/or likelihood of survival. For this purpose, and by way of example, RNA is extracted from a cell or tissue sample, the small RNAs (18-26-nucleotide RNAs) are size-selected from total RNA using denaturing polyacrylamide gel electrophoresis (PAGE). Then oligonucleotide linkers are attached to the 5' and 3' ends of the small RNAs and the resulting ligation products are used as templates for an RT-PCR reaction with 10 cycles of amplification. The sense strand PCR primer has a Cy3 fluorophore attached to its 5' end, thereby fluorescently labelling the sense strand of the PCR product. The PCR product is denatured and then hybridized to the microarray. A PCR product, referred to as the target nucleic acid that is complementary to the corresponding RNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular biomarker, using a number of positive and negative controls and array data normalization methods, which will result in assessment of the level of expression of a particular biomarker.

Several types of microarrays can be employed such as spotted oligonucleotide microarrays, pre-fabricated oligonucleotide microarrays or spotted long oligonucleotide arrays. In spotted oligonucleotide microarrays the capture probes are oligonucleotides complementary to nucleic acid sequences. This type of array is typically hybridized with amplified. PCR products of size-selected small RNAs from two samples to be compared that are labelled with two different fluorophores. Alternatively, total RNA containing the small RNA fraction is extracted from the abovementioned two samples and used directly without size-selection of small RNAs, and 3' end labeled using T4 RNA ligase and short RNA linkers labelled with two different fluorophores. The samples can be mixed and hybridized to one single microarray that is then scanned, allowing the visualization of up-regulated and down-regulated biomarker genes in one go. The downside of this is that the absolute levels of gene expression cannot be observed, but the cost of the experiment is reduced by half. Alternatively, a universal reference can be used, comprising of a large set of fluorophore-labelled oligonucleotides, complementary to the array capture probes.

In pre-fabricated oligonucleotide microarrays or single-channel microarrays, the probes are designed to match the sequences of known or predicted biomarkers. There are commercially available designs that cover complete genomes from companies such as Affymetrix, or Agilent. These microarrays give estimations of the absolute value of gene expression and therefore the comparison of two conditions requires the use of two separate microarrays.

Spotted long oligonucleotide arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing. More recently, Maskless Array Synthesis from NimbleGen Systems has combined flexibility with large numbers of probes. Arrays can contain up to 390,000 spots, from a custom array design.

An embodiment of the present disclosure concerns the method of microarray use and analysis as described herein.

The terms "PCR reaction", "PCR amplification", "PCR", "pre-PCR", "Q-PCR", "real-time quantitative PCR" and "real-time quantitative RT-PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence based amplification and Q Beta Replicase systems. The products formed by said amplification reaction may or may not be monitored in real time or only after the reaction as an end-point measurement.

Real-time quantitative RT-PCR is a modification of polymerase chain reaction used to rapidly measure the quantity of a product of polymerase chain reaction. It is preferably done in real-time, thus it is an indirect method for quantitatively measuring starting amounts of DNA, complementary DNA or ribonucleic acid (RNA). This is commonly used for the purpose of determining whether a genetic sequence is present or not, and if it is present the number of copies in the sample. There are 3 methods which vary in difficulty and detail. Like other forms of polymerase chain reaction, the process is used to amplify DNA samples, using thermal cycling and a thermostable DNA polymerase.

The three commonly used methods of quantitative polymerase chain reaction are through agarose gel electrophoresis, the use of SYBR Green, a double stranded DNA dye, and the fluorescent reporter probe. The latter two of these three can be analysed in real-time, constituting real-time polymerase chain reaction method.

Agarose gel electrophoresis is the simplest method, but also often slow and less accurate then other methods, depending on the running of an agarose gel via electrophoresis. It cannot give results in real time. The unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown. This method is generally used as a simple measure of whether the probe target sequences are present or not, and rarely as 'true' Q-PCR.

Using SYBR Green dye is more accurate than the gel method, and gives results in real time. A DNA binding dye binds all newly synthesized double stranded (ds)DNA and an increase in fluorescence intensity is measured, thus allowing initial concentrations to be determined. However, SYBR Green will label all dsDNA including any unexpected PCR products as well as primer dimers, leading to potential complications and artifacts. The reaction is prepared as usual, with the addition of fluorescent dsDNA dye. The reaction is run, and the levels of fluorescence are monitored; the dye only fluoresces when bound to the dsDNA. With reference to a standard sample or a standard curve, the dsDNA concentration in the PCR can be determined. The fluorescent reporter probe method is the most accurate and most reliable of the methods. It uses a sequence-specific nucleic acid based probe so as to only quantify the probe sequence and not all double stranded DNA. It is commonly carried out with DNA based probes with a fluorescent reporter and a quencher held in adjacent positions, so-called dual-labelled probes. The close proximity of the reporter to the quencher prevents its fluorescence; it is only on the breakdown of the probe that the fluorescence is detected. This process depends on the 5' to 3' exonuclease activity of the polymerase involved. The real-time quantitative PCR reaction is prepared with the addition of the dual-labelled probe. On denaturation of the double-stranded DNA template, the probe is able to bind to its complementary sequence in the region of interest of the template DNA (as the primers will too). When the PCR reaction mixture is heated to activate the polymerase, the polymerase starts synthesizing the complementary strand to the primed single stranded template DNA. As the polymerisation continues it reaches the probe bound to its complementary sequence, which is then hydrolysed due to the 5'-3' exonuclease activity of the polymerase thereby separating the fluorescent reporter and the quencher molecules. This results in an increase in fluorescence, which is detected. During thermal cycling of the real-time PCR reaction, the increase in fluorescence, as released from the hydrolysed dual-labelled probe in each PCR cycle is monitored, which allows accurate determination of the final, and so initial, quantities of DNA.

Any method of PCR that can determine the expression of a nucleic acid molecule as defined herein falls within the scope of the present disclosure. A preferred embodiment of the present disclosure includes the real-time quantitative RT-PCR method, based on the use of either SYBR Green dye or a dual-labelled probe for the detection and quantification of nucleic acids according to the herein described.

An aspect of the present disclosure includes the detection of the nucleic acid molecules herein disclosed by techniques such as Northern blot analysis. Many variations of the protocol exist.

The following examples are offered by way of illustration and not by way of limitation.

EXAMPLES

Example 1

High-grade serous ovarian carcinoma (HGSC) is an aggressive type of epithelial ovarian cancer (EOC) associated with numerous genetic alterations and poor survival. An important clinical question is how to identify ovarian cancer patients that are most likely to benefit from anti-angiogenic specific therapy. There is a need to develop novel prognostic biomarkers of angiogenesis that can be used to identify patients that will benefit from antiangiogenic therapies. Until such biomarkers are identified patients who will truly benefit from the antiangiogenic treatments will be missed and some will be subjected to unnecessary toxicity and health care costs associated with those treatments. The objective of the study described herein was to identify novel angiogenic biomarkers that are associated with clinical outcome in women with HGSC. Specifically, this study was designed to investigate the association between angiogenic gene expression profiles and overall survival (OS) in women with HGSCs. In this study several novel and unreported angiogenic genes were identified that are associated with survival in women with HGSCs.

Between 1988 and 2001 under an IRB approved protocol, 65 serous ovarian cancer patients were enrolled for an IRB-approved clinical trial at Duke University Medical Center (Durham, N.C.). The patients were treated at Duke University Medical Center. A platin-based combination chemotherapy was used for all the stage III/IV cases.

The cancer specimens were collected and snap-frozen at initial surgery before any chemotherapy. All pretreatment biopsies were confirmed to have at least 60% invasive disease throughout the core sample before RNA harvesting. RNA was prepared, and probes were generated and used for hybridization to AFFYMETRIX U133A GENECHIP ARRAYS as has been described previously in detail (Berchuck, Iversen et al. 2005, Berchuck, Iversen et al. 2009).

The focus for this study was a subcohort of 51 patients who were considered HGSC (stage III A, B, C and IV, grade 2 and 3). The original study had an extreme phenotyping design, so samples from women who had either long or short overall survival (OS) times were identified. Long term survival was defined as OS of 7 years or more vs. short term survival was defined as OS of 3 years or less (Berchuck et al., 2005). Median survival and follow-up times were 33 and 184 months, respectively.

One hundred forty five angiogenic candidate genes were identified based on literature review. A panel of 285 probe sets (features) linked to 145 genes involved in angiogenesis were screened. A panel of 285 probe sets linked to HUGO Gene Nomenclature Committee (HGNC) gene symbols using annotation data from public databases and a chip annotation file from the Bioconductor package was derived (Gentleman, R C, et al., 2004).

Microvessel density (MVD) counts, surrogates of angiogenesis, were determined using CD31 and CD105, markers of proliferating endothelial cells. MVD analysis using CD31 and CD105 markers was performed as previously described. (Rubatt. Darcy et al. 2009). Briefly, five micrometer sections of formalin-fixed, paraffin-embedded tissue were stained using monoclonal antibodies to CD31 (JC70A; DakoCytomation, Glostrup, Denmark) and CD105 (SN6h; DakoCytomation, Carpinteria, Calif.). For negative control, mouse IgG was used. For positive control an ovarian cancer specimen known to exhibit a high degree of angiogenesis and liver parenchyma was used. The 4PLUS IMMUNOPEROXIDASE DETECTION SYSTEM (Biocare Medical, Concord, Calif.) and CATALYZED SIGNAL AMPLIFICATION SYSTEM (DakoCytomation, Carpinteria, Calif.) were used for CD31 and CD105 staining, respectively.

The association between mRNA expression levels and overall survival (OS) was assessed using a rank score statistic. The effect size was estimated parametrically as a hazard ratio (HR) under a proportional hazards model. Multiple testing was accounted for within the false-discovery rate (FDR) framework using the Storey q-value method. The associations between expression level and OS for the implicated genes were further assessed in a published HGSC cohort from the "The Cancer Genome Atlas" (TCGA) database and the "Genomic Spatial Event" (GSE).

The TCGA mRNA data were retrieved from the Cancer Genomic Data Server (CGDS) through the Computational Biology Center Portal (cBio): http://www.cbioportal.org/. The cdgsr extension package (cran.rproject.org/web/packages/cgdsr/) was used to execute the retrieval. In addition to the TCGA database, the panel of the 31 biomarkers were analyzed in 11 publically available databases as described in Bentink et al., 2012. Five of the databases (GSE26712 (Bonome, T et al., 2008), GSE18520 (Mok, S C et al., 2009), GSE14764 (Denkert, C et al., 2009), GSE 17260 (Yoshihara, K et al. 2010), and GSE 19161 (Zhang, L et al., 2008) included information on women with advanced HGSC and the number of cases in the data bases matched the 2012 Bentink el al. paper. For the TCGA and GSE databases, only unadjusted p-values are reported.

Association between gene expression of each probe set and OS was assessed using a rank score test (Owzar, K et al., 2011). Corresponding effect size was quantitatively assessed using a hazard ratio assuming proportional hazards. Conditional inference trees were used to find optimal cutpoints (Hothorn T et al., 2006). Multiplicity was addressed within the False Discovery Rate (FDR) framework. FDR adjusted P-values (Q-values) were calculated using a method by Storey (Owzar, K et al., 2011). All analyses were performed using the R Statistical Environment and extension packages from CRAN and the Bioconductor project (Owzar, K et al., 2011).

Statistical Analysis and Validation of Microarray Results:

The study was begun with 145 angiogenic candidate genes based on literature review. A panel of 285 probe sets on the array linked to candidate markers involved in angiogenesis were screened. The AFFYMETRIX hgu133a arrays were pre-processed using the RMA [Bolstad et al] algorithm. (Bolstad, Irizarry et al. 2003). Probe sets were linked to HGNC gene names using annotation data from public databases and a chip annotation file from the Bioconductor package. The TCGA mRNA data were retrieved from the Cancer Genomic Data Server (CGDS) through the Computational Biology Center Portal (cBio): http://www.cbioportal.org/. The cdgsr extension package (cran.rproject.org/web/packages/cgdsr/) was used to execute the retrieval. Association between gene expression of each probe set and OS was assessed using a rank score test [Jung et al; 2005]. Corresponding effect size was quantitatively assessed using a hazard ratio assuming proportional hazards. Conditional inference trees [Hothorn et al; 2006] were used to find optimal cutpoints. Multiplicity was addressed within the False Discovery Rate (FDR) framework False-Discovery Rate (FDR) adjusted P-values (Q-values) were calculated using a method by Storey [2002]. All analyses were performed using the R Statistical Environment and extension packages from CRAN and the Bioconductor Package.

Results:

The results of the study demonstrated an association between differential angiogenic gene expression and survival in HGSC. Specifically, forty-three features (Affymetrix probesets) linked to 31 angiogenic associated genes were significantly associated OS (FDR q-value (q)<0.05) (see Table 1 and FIGS. 1-31). FIGS. 1-31 are box graphs for the 31 biomarkers showing that a higher expression level of the biomarker is associated with overall survival (OS) time (either Long: 7 years or more, or Short: 3 years or less) in HGSC patients. A higher expression level of the biomarkers EPHB2, ERBB2, FLT1, PF4, NRP1, COL4A3, ANGPTL3, ANGPT4, CSF3, CUL7, F2, FOXC2, HGF, HSPG2, ILSRA, ITGB3, LECT1, NOS3, NRP1, PLG, TGFA, and TNNI1 are associated with a likely shorter OS and a higher expression level of the biomarkers AKT1, CD44, F3, GUSB, HIF1A, HPRT1, IL8, JAG1, TEK, and VASH1 are associated with a likely longer OS.

In addition, 4 of the 31 genes were confirmed in the TCGA database, exhibiting level of significance and concordant direction of effect: V-Akt Murine Thymoma Viral Oncogene Homolog 1 (AKT1) (q=0.018; TCGA unadjusted p-value <0.01, HR=0.81), CD44 molecule (CD44) (q-value <0.003; TCGA p-value <0.05, HR=0.89), Ephrin Receptor B2 (EPHB2) (q-value <0.009; TCGA p<0.05, HR=1.23) and V-erb-b2 Avian Erythroblastic Leukemia Viral Oncogene Homolog 2 (ERBB2/HER2) (q-value <0.019; TCGA p-value <0.05, HR=1.19) (see FIGS. 32-35).

AKT (or Protein Kinase B, PKB):

The data described herein indicate that lower expression of AKT is associated with worse overall survival (see FIG. 1 and FIG. 32). Median survival of 98 months was observed for high expression versus 22.5 months for low expression levels (p<0.003, q-value=0.02, HR=0.4, TCGA p-value=0.01, HR=0.8).

Figures 33A, 33B:
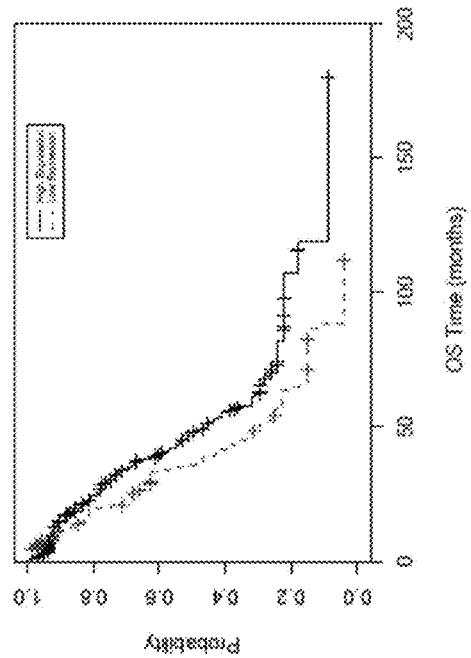
FIGS. 33A-33B are graphs for biomarker CD44 showing an association between increased gene expression levels of the biomarker and overall survival (OS) time in accordance with one or more embodiments of the present disclosure. A) A box graph of data collected from a study conducted at Duke University showing that a higher expression level of the biomarker CD44 is associated with an increase in OS of 7 years or more. B) A graph of probability versus OS time for high expression (solid line) and low expression (dashed line) of the biomarker CD44 using data from the publically available database "The Cancer Genome Atlas" (TCGA) confirming the direction of the association shown in (A) which is higher expression levels of CD44 associated with longer OS.
Figures 36A, 36B, 37A, 37B:
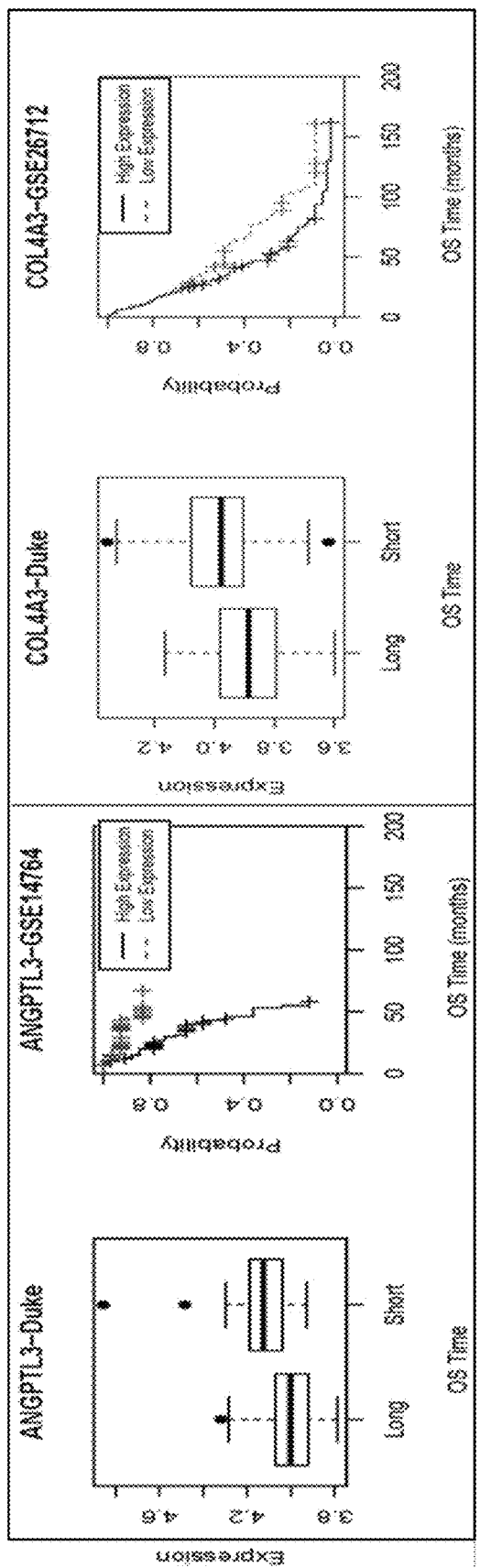
FIGS. 36A-36B are graphs for biomarker ANGPTL3 showing an association between increased gene expression levels of the biomarker and overall survival (OS) time in accordance with one or more embodiments of the present disclosure. A) A box graph of data collected from a study conducted at Duke University showing that a higher expression level of the biomarker ANGPTL3 is associated with a decrease in OS of 3 years or less. B) A graph of probability versus OS time for high expression (solid line) and low expression (dashed line) of the biomarker ANGPTL3 using data from the publically available database "Genomic Spatial Event" (GSE) and, in particular, GSE database GSE14764 confirming the direction of the association shown in (A) which is higher expression levels of ANGPTL3 associated with shorter OS.
FIGS. 37A-37B are graphs for biomarker COL4A3 showing an association between increased gene expression levels of the biomarker and overall survival (OS) time in accordance with one or more embodiments of the present disclosure. A) A box graph of data collected from a study conducted at Duke University showing that a higher expression level of the biomarker COL4A3 is associated with a decrease in OS of 3 years or less. B) A graph of probability versus OS time for high expression (solid line) and low expression (dashed line) of the biomarker COL4A3 using data from the publically available database "Genomic Spatial Event" (GSE) and, in particular, GSE databases GSE26712 and GSE14764 confirming the direction of the association shown in (A) which is higher expression levels of COL4A3 associated with shorter OS.
Figures 38A, 38B, 39A, 39B:
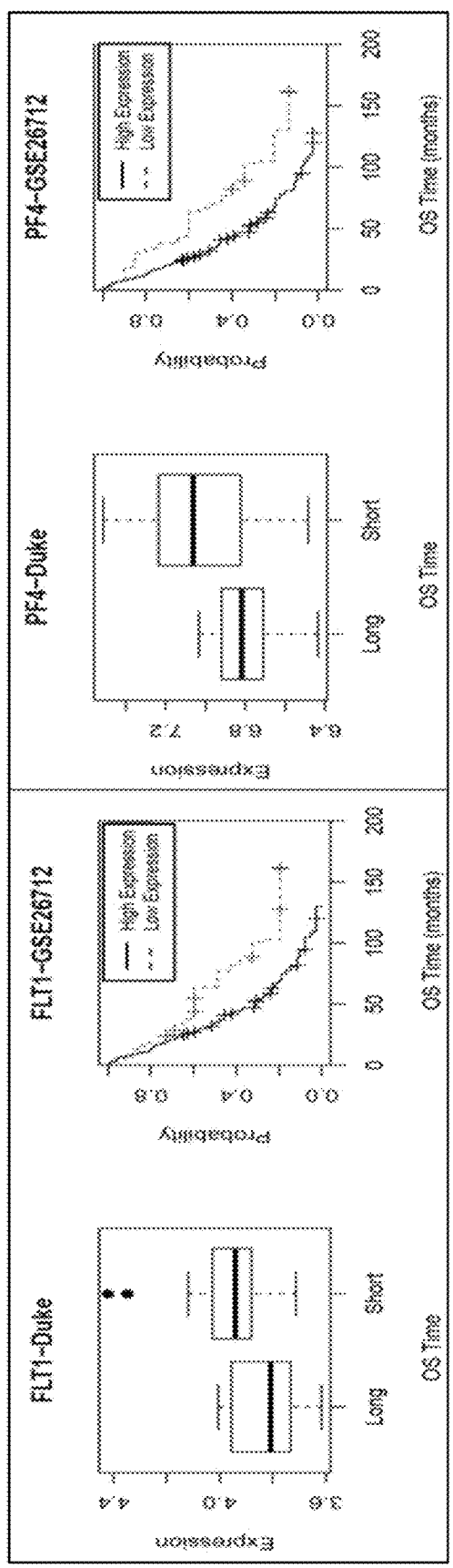
FIGS. 38A-38B are graphs for biomarker FLT1 showing an association between increased gene expression levels of the biomarker and overall survival (OS) time in accordance with one or more embodiments of the present disclosure. A) A box graph of data collected from a study conducted at Duke University showing that a higher expression level of the biomarker FLT1 is associated with a decrease in OS of 3 years or less. B) A graph of probability versus OS time for high expression (solid line) and low expression (dashed line) of the biomarker FLT1 using data from the publically available database "Genomic Spatial Event" (GSE) and, in particular, GSE databases GSE26712 and GSE14764 confirming the direction of the association shown in (A) which is higher expression levels of FLT1 associated with shorter OS.
FIGS. 39A-39B are graphs for biomarker PF4 showing an association between increased gene expression levels of the biomarker and overall survival (OS) time in accordance with one or more embodiments of the present disclosure. A) A box graph of data collected from a study conducted at Duke University showing that a higher expression level of the biomarker PF4 is associated with a decrease in OS of 3 years or less. B) A graph of probability versus OS time for high expression (solid line) and low expression (dashed line) of the biomarker PF4 using data from the publically available database "Genomic Spatial Event" (GSE) and, in particular, GSE databases GSE26712 and GSE14764 confirming the direction of the association shown in (A) which is higher expression levels of PF4 associated with shorter OS.
Figures 40A, 40B:
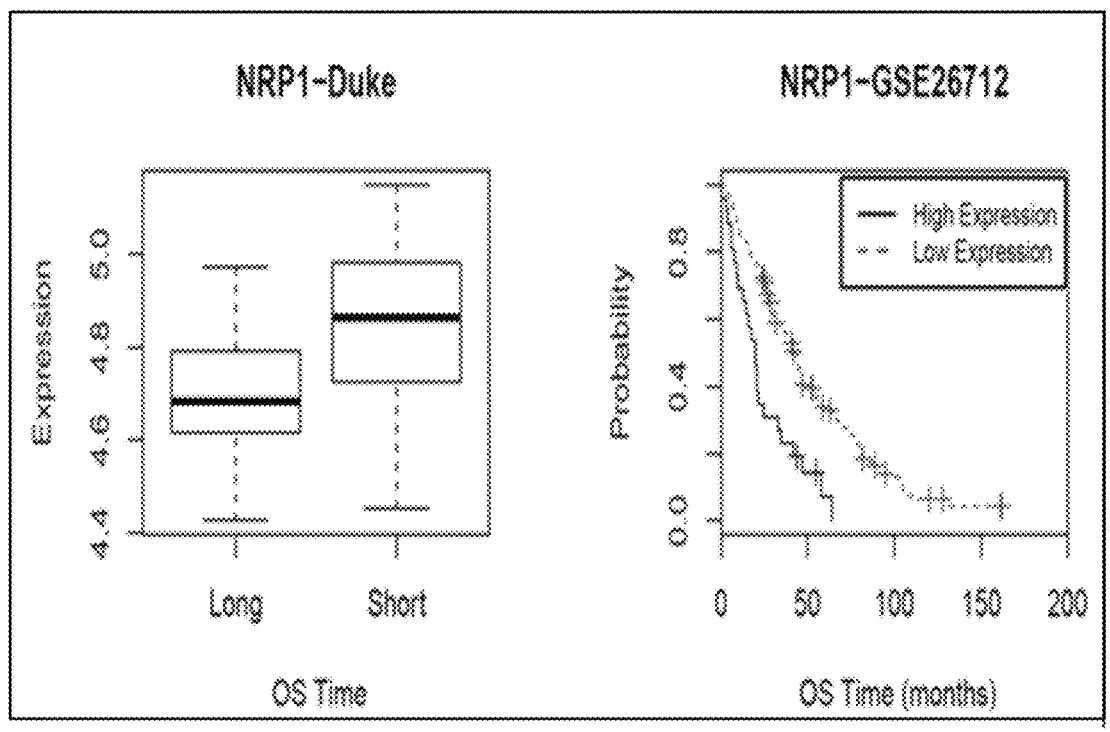
FIGS. 40A-40B are graphs for biomarker NRP1 showing an association between increased gene expression levels of the biomarker and overall survival (OS) time in accordance with one or more embodiments of the present disclosure. A) A box graph of data collected from a study at Duke University showing that a higher expression level of the biomarker NRP1 is associated with a decrease in OS of 3 years or less. B) A graph of probability versus OS time for high expression (solid line) and low expression (dashed line) of the biomarker NRP1 using data from the publically available database "Genomic Spatial Event" (GSE) and, in particular, GSE databases GSE26712 and GSE14764 confirming the direction of the association shown in (A) which is higher expression levels of NRP1 associated with shorter OS.
Figure 41:
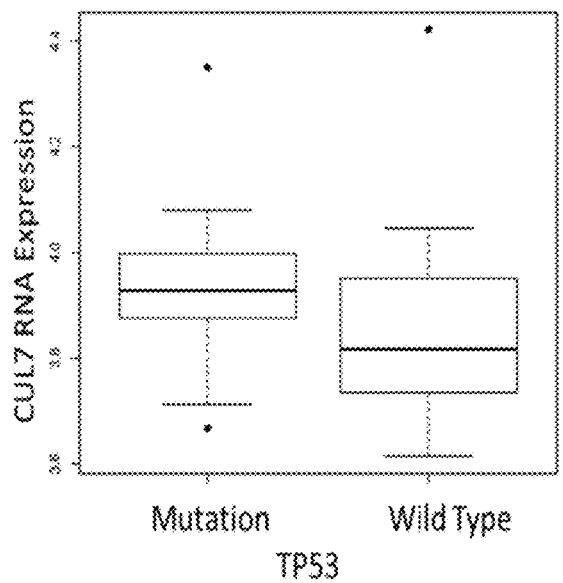
FIG. 41 is a box graph for biomarker CUL7 showing an association between increased RNA expression levels of the biomarker and TP53 (P53) mutation status in accordance with one or more embodiments of the present disclosure. This figure shows that tumors with higher levels of CUL7 expression have more P53 mutations (Mutation) than P53 wild type (Wild Type).
Figure 42:
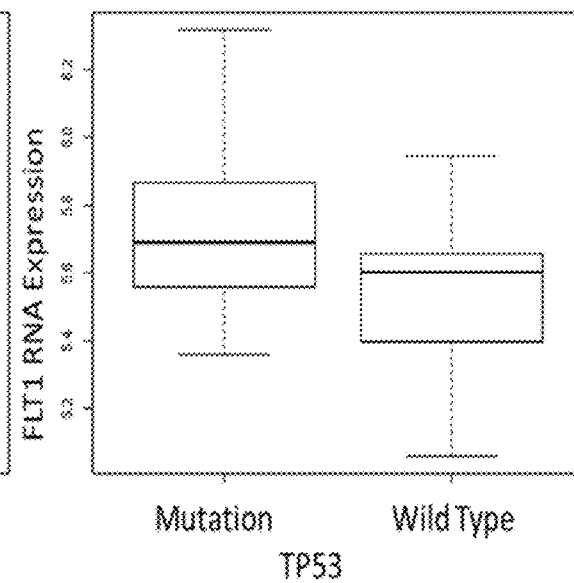
FIG. 42 is a box graph for biomarker FLT1 showing an association between increased RNA expression levels of the biomarker and TP53 (P53) mutation status in accordance with one or more embodiments of the present disclosure. This figure shows that tumors with higher levels of FLT1 expression have more P53 mutations (Mutation) than P53 wild type (Wild Type).
Figure 43:
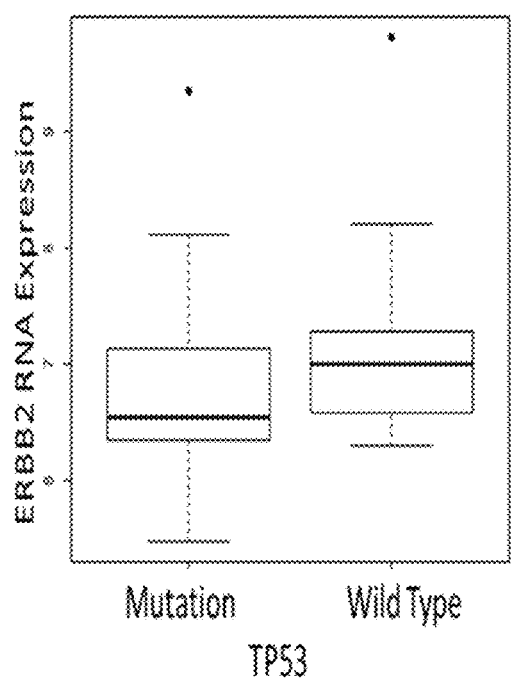
FIG. 43 is a box graph for biomarker ERBB2 showing an association between increased RNA expression levels of the biomarker and TP53 (P53) mutation status in accordance with one or more embodiments of the present disclosure. This figure shows that tumors with higher levels of ERBB2 expression have more P53 wild type (Wild Type) than P53 mutations (Mutation).
Figure 44:
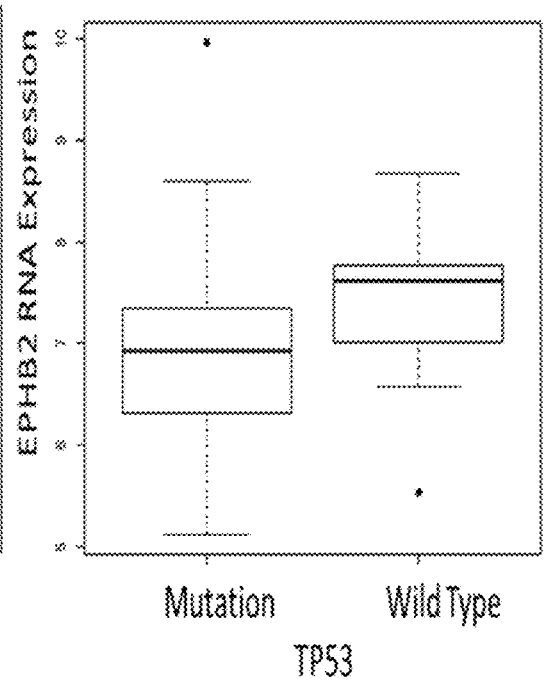
FIG. 44 is a box graph for biomarker EPHB2 showing an association between increased RNA expression levels of the biomarker and TP53 (P53) mutation status in accordance with one or more embodiments of the present disclosure. This figure shows that tumors with higher levels of EPHB2 expression have more P53 wild type (Wild Type) than P53 mutations (Mutation).
Figure 45:
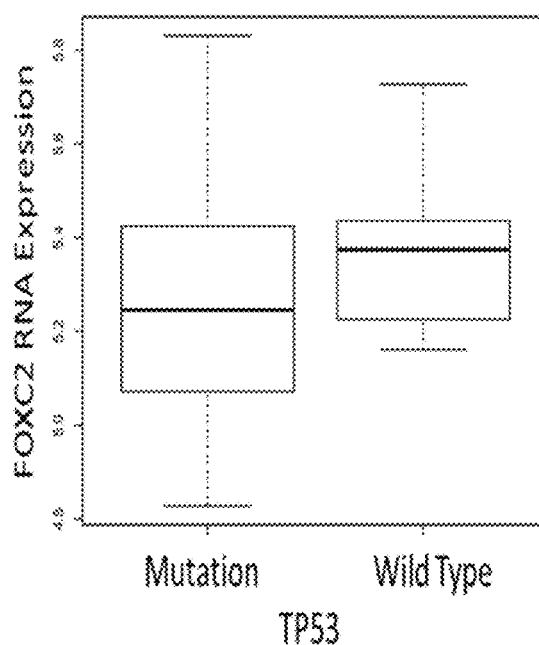
FIG. 45 is a box graph for biomarker FOXC2 showing an association between increased RNA expression levels of the biomarker and TP53 (P53) mutation status in accordance with one or more embodiments of the present disclosure. This figure shows that tumors with higher levels of FOXC2 expression have more P53 wild type (Wild Type) than P53 mutations (Mutation).
Figure 46:
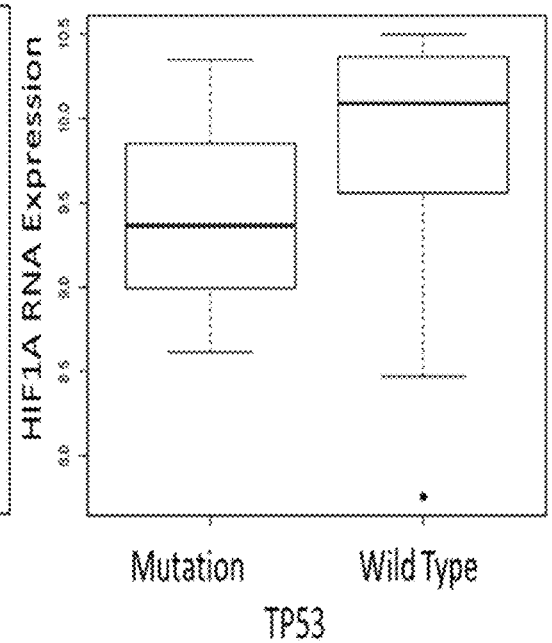
FIG. 46 is a box graph for biomarker HIF1A showing an association between increased RNA expression levels of the biomarker and TP53 (P53) mutation status in accordance with one or more embodiments of the present disclosure. This figure shows that tumors with higher levels of HIF1A expression have more P53 wild type (Wild Type) than P53 mutations (Mutation).
Figure 47:
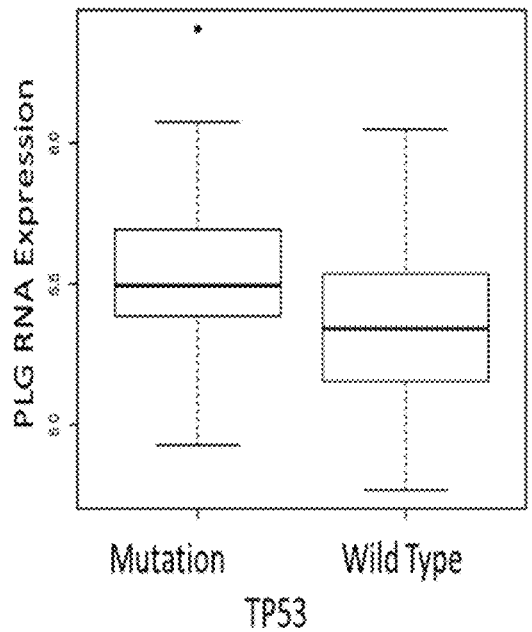
FIG. 47 is a box graph for biomarker PLG showing an association between increased RNA expression levels of the biomarker and TP53 (P53) mutation status in accordance with one or more embodiments of the present disclosure. This figure shows that tumors with higher levels of PLG expression have more P53 mutations (Mutation) than P53 wild type (Wild Type).
Figure 48:
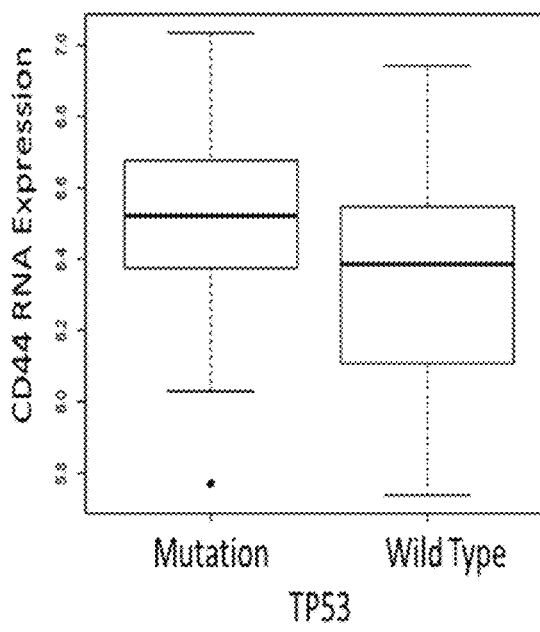
FIG. 48 is a box graph for biomarker CD44 showing an association between increased RNA expression levels of the biomarker and TP53 (P53) mutation status in accordance with one or more embodiments of the present disclosure. This figure shows that tumors with higher levels of CD44 expression have more P53 mutations (Mutation) than P53 wild type (Wild Type).

CD 44:

In the study, the high expression levels of CD 44 was associated with improved OS with a median overall survival of 119.0 months compared to the 23.5 month overall survival for low expression levels (p=2.846e$^{-05}$, q-value=0.003, HR=0.5, TCGA p-value=0.5, HR=0.9), as seen in FIG. 2 and FIG. 33).

EPH Receptor B2 (EPHB2):

The results described herein indicate the reduced overall survival in patients with higher expression of EphB2 (FIG. 8 and FIG. 35). The EPHB2 high expression was associated with a median of 22.5 months overall survival in HGSC versus 103.0 months median overall survival in patients with lower EPHB2 expression (p<0.0006, q-value=0.009, HR=8.1, TCGA p-value=0.05, HR=1.2).

ERBB2/HER2:

In this study population the high expression of ERBB2/HER2 was associated with a median of 22 months overall survival versus 91 months median overall survival in patients with lower ERBB2 expressions as shown in FIG. 9 and FIG. 34 (p<0.003; FIG. 3, q-value=0.019, HR=2.9, TCGA p-value=0.055, HR=1.2); leading to the conclusion that there is a reduced overall survival in patients with higher expression of ERBB2.

Further, in the GSE databases, 5 common genes were identified (see FIGS. 36-40): Fms-like tyrosine kinase 1 (FLT1, also known as VEGFR1) (q-value=0.03; GSE26712 p-value=0.01, HR=3.09); platelet factor 4 (PF4: q-value=0.02; GSE26712 p-value=0.01, HR=3.03), Neuropilin 1 (NRP1: q-value=0.02; GSE26712 p-value <0.04, HR>1.37), Collagen, Type IV, Alpha-3 (COL4A3: q-value <0.019; GSE26712 p-value=0.03, HR=1.30), and Angiopoietin-like 3 (ANGPTL3). High expression of FLT1, PF4, NRP1, COL4A3, and ANGPTL3 were associated with shorter survival.

In addition to the data described above, the 31 biomarker genes shown in Table 1 were further analyzed for an association with TP53(P53) mutation status and the data are shown in FIGS. 41-48 and Table 2. The results indicated that there is a significant association between gene expression levels in a subset of the 31 angiogenic related genes and overall survival (OS). Specifically, 8 of the biomarker genes had significant association with P53 mutation status (p-value ≤0.05). Biomarker genes CUL7, FLT1, PLG, and CD44 had a significant association with P53 mutation status. A higher expression level of CUL7, FLT1, and PLG was associated with shorter overall survival, in addition to these biomarker genes also showing a significant association with P53 mutation status, which status can be a separate indicator of tumor aggressiveness.

REFERENCES

Alvarez, A. A., H. R. Krigman, R. S. Whitaker, R. K. Dodge and G. C. Rodriguez (1999). "The prognostic significance of angiogenesis in epithelial ovarian carcinoma." Clin Cancer Res 5(3): 587-591.

Arai, T., J. S. Kasper, J. R. Skaar, S. H. Ali, C. Takahashi and J. A. DeCaprio (2003). "Targeted disruption of p185/Cul7 gene results in abnormal vascular morphogenesis." Proceedings of the National Academy of Sciences 100(17): 9855-9860.

Bast, R. C., Jr., B. Hennessy and G. B. Mills (2009). "The biology of ovarian cancer: new opportunities for translation." Nature Reviews Cancer 9(6): 415-428.

Bellacosa, A., C. C. Kumar, A. D. Cristofano and J. R. Testa (2005). Activation of AKT Kinases in Cancer: Implications for Therapeutic Targeting. Advances in Cancer Research. F. V. W. George and K. George, Academic Press. Volume 94: 29-86.

Berchuck, A., E. S. Iversen, J. M. Lancaster, J. Pittman, J. Luo, P. Lee, S. Murphy, H. K. Dressman, P. G. Febbo, M. West, J. R. Nevins and J. R. Marks (2005). "Patterns of Gene Expression That Characterize Long-term Survival in Advanced Stage Serous Ovarian Cancers." Clinical Cancer Research 11(10): 3686-3696.

Bentink S, Haibe-Kains B, Risch T, Fan J B, Hirsch M S, et al. (2012) Angiogenic mRNA and microRNA gene expression signature predicts a novel subtype of serous ovarian cancer. PLoS One 7: e30269.

Berchuck, A., E. S. Iversen, J. M. Lancaster, J. Pittman, J. Luo, P. Lee, S. Murphy, H. K. Dressman, P. G. Febbo, M. West, J. R. Nevins and J. R. Marks (2005). "Patterns of gene expression that characterize long-term survival in advanced stage serous ovarian cancers." Clin Cancer Res 11(10): 3686-3696.

Berchuck, A., E. S. Iversen, J. Luo, J. P. Clarke, H. Home, D. A. Levine, J. Boyd, M. A. Alonso, A. A. Secord, M. Q. Bernardini, J. C. Barnett, T. Boren, S. K. Murphy, H. K. Dressman, J. R. Marks and J. M. Lancaster (2009). "Microarray analysis of early stage serous ovarian cancers shows profiles predictive of favorable outcome." Clin Cancer Res 15(7): 2448-2455.

Berchuck A, Iversen E S, Lancaster J M, Pittman J, Luo J, et al. (2005) Patterns of gene expression that characterize long-term survival in advanced stage serous ovarian cancers. Clin Cancer Res 11: 3686-3696.

Berclaz, G., B. Flutsch, H. J. Altermatt, V. Rohrbach, V. Djonov, A. Ziemiecki, E. Dreher and A. C. Andres (2002). "Loss of EphB4 receptor tyrosine kinase protein expression during carcinogenesis of the human breast." Oncol Rep 9(5): 985-989.

Bojesen, S. E., S. K. Kjaer, E. V. Hogdall, B. L. Thomsen, C. K. Hogdall, J. Blaakaer, A. Tybjaerg-Hansen and B. G. Nordestgaard (2005). "Increased risk of ovarian cancer in integrin beta3 Leu33Pro homozygotes." Endocr Relat Cancer 12(4): 945-952.

Bolstad, B. M., R. A. Irizarry, M. Åstrand and T. P. Speed (2003). "A comparison of normalization methods for high density oligonucleotide array data based on variance and bias." Bioinformatics 19(2): 185-193.

Bonome T, Levine D A, Shih J, Randonovich M, Pise-Masison C A, et al. (2008) A gene signature predicting for survival in suboptimally debulked patients with ovarian cancer. Cancer Res 68: 5478-5486.

Bose, S., S. Chandran, J. M. Mirocha and N. Bose (2005). "The Akt pathway in human breast cancer: a tissue-array-based analysis." Mod Pathol 19(2): 238-245.

Burger, R. A. (2007). "Experience with bevacizumab in the management of epithelial ovarian cancer." J Clin Oncol 25(20): 2902-2908.

Burger, R. A. (2011). "Antiangiogenic agents should be integrated into the standard treatment for patients with ovarian cancer." Ann Oncol 22 Suppl 8: viii65-viii68.

Cheng, J. Q., A. K. Godwin, A. Bellacosa, T. Taguchi, T. F. Franke, T. C. Hamilton, P. N. Tsichlis and J. R. Testa (1992). "AKT2, a putative oncogene encoding a member of a subfamily of protein-serine/threonine kinases, is amplified in human ovarian carcinomas." Proc Natl Acad Sci USA 89(19): 9267-9271.

Collins, A. T., P. A. Berry, C. Hyde, M. J. Stower and N. J. Maitland (2005). "Prospective identification of tumorigenic prostate cancer stem cells." Cancer Res 65(23): 10946-10951.

Combaret, V., C. Lasset, D. Frappaz, R. Bouvier, P. Thiesse, A. C. Rebillard, T. Philip and M. C. Favrot (1995). "Evaluation of CD44 prognostic value in neuroblastoma: Comparison with the other prognostic factors." European Journal of Cancer 31(4): 545-549.

Dalerba, P., S. J. Dylla, I. K. Park, R. Liu, X. Wang, R. W. Cho, T. Hoey, A. Gurney, E. H. Huang, D. M. Simeone, A. A. Shelton, G. Parmiani, C. Castelli and M. F. Clarke (2007). "Phenotypic characterization of human colorectal cancer stem cells." *Proc Natl Acad Sci USA* 104(24): 10158-10163.

de Jong, J. S., P. J. van Diest and J. P. Baak (2000). "Hot spot microvessel density and the mitotic activity index are strong additional prognostic indicators in invasive breast cancer." *Histopathology* 36(4): 306-312.

Denkert C, Budczies J, Darb-Esfahani S, Gyorffy B, Sehouli J, et al. (2009) A prognostic gene expression index in ovarian cancer—validation across different independent data sets. J Pathol 218: 273-280.

Derynck, R., A. B. Roberts, M. E. Winkler, E. Y. Chen and D. V. Goeddel (1984). "Human transforming growth factor-alpha: precursor structure and expression in *E. coli.*" *Cell* 38(1): 287-297.

Fillmore, C. M. and C. Kuperwasser (2008). "Human breast cancer cell lines contain stem-like cells that self-renew, give rise to phenotypically diverse progeny and survive chemotherapy." *Breast Cancer Res* 10(2): R25.

Folkman, J. (1994). "Angiogenesis and breast cancer." *Journal of Clinical Oncology* 12(3): 441-443.

Folkman, J. (2002). "Role of angiogenesis in tumor growth and metastasis." *Seminars in Oncology* 29(6): 15-18.

Gentleman R C, Carey V J, Bates D M, Bolstad B, Dettling M, et al. (2004) Bioconductor: open software development for computational biology and bioinformatics. Genome Biology 5.

Hiratsuka, S., Y. Maru, A. Okada, M. Seiki, T. Noda and M. Shibuya (2001). "Involvement of Flt-1 tyrosine kinase (vascular endothelial growth factor receptor-1) in pathological angiogenesis." *Cancer Res* 61(3): 1207-1213.

Hlatky, L., P. Hahnfeldt and J. Folkman (2002). "Clinical application of antiangiogenic therapy: microvessel density, what it does and doesn't tell us." *J Natl Cancer Inst* 94(12): 883-893.

Hothorn T, Hornik K, Zeileis A (2006) Unbiased recursive partitioning: A conditional inference framework. Journal of Computational and Graphical Statistics 15: 651-674.

Indumathi, S., R. Harikrishnan, J. S. Rajkumar, D. Sudarsanam and M. Dhanasekaran (2013). "Prospective biomarkers of stem cells of human endometrium and fallopian tube compared with bone marrow." *Cell Tissue Res.*

Jones, N., K. Iljin, D. J. Dumont and K. Alitalo (2001). "Tie receptors: new modulators of angiogenic and lymphangiogenic responses." *Nat Rev Mol Cell Biol* 2(4): 257-267.

Jung, P., B. Verdoodt, A. Bailey, J. R. Yates, A. Menssen and H. Hermeking (2007). "Induction of Cullin 7 by DNA damage attenuates p53 function." *Proceedings of the National Academy of Sciences* 104(27): 11388-11393.

Kim, S. S., M. Shago, L. Kaustov, P. C. Boutros, J. W. Clendening, Y. Sheng, G. A. Trentin, D. Barsyte-Lovejoy, D. Y. L. Mao, R. Kay, I. Jurisica, C. H. Arrowsmith and L. Z. Penn (2007). "CUL7 Is a Novel Antiapoptotic Oncogene." *Cancer Research* 67(20): 9616-9622.

Kyama, C. M., L. Overbergh, A. Mihalyi, C. Meuleman, J. M. Mwenda, C. Mathieu and T. M. D'Hooghe (2008). "Endometrial and peritoneal expression of aromatase, cytokines, and adhesion factors in women with endometriosis." *Fertil Steril* 89(2): 301-310.

Lee, J. and P. Zhou (2010). "Cullins and cancer." *Genes Cancer* 1(7): 690-699.

Loges, S., T. Schmidt and P. Carmeliet (2010). "Mechanisms of resistance to anti-angiogenic therapy and development of third-generation anti-angiogenic drug candidates." *Genes Cancer* 1(1): 12-25.

Maeda, Y., T. Suzuki, X. F. Pan, G. Chen, S. Q. Pan, T. Bartman and J. A. Whitsett (2008). "CUL2 is required for the activity of hypoxia-inducible factor and vasculogenesis." *Journal of Biological Chemistry* 283(23): 16084-16092.

Maksimova, N., K. Hara, A. Miyashia, I. Nikolaeva, A. Shiga, A. Nogovicina, A. Sukhomyasova, V. Argunov, A. Shvedova, T. Ikeuchi, M. Nishizawa, R. Kuwano and O. Onodera (2007). "Clinical, molecular and histopathological features of short stature syndrome with novel CUL7 mutation in Yakuts: new population isolate in Asia." *J Med Genet* 44(12): 772-778.

May, K. E., J. Villar, S. Kirtley, S. H. Kennedy and C. M. Becker (2011). "Endometrial alterations in endometriosis: a systematic review of putative biomarkers." *Hum Reprod Update* 17(5): 637-653.

Miyazaki, T., H. Kato, M. Fukuchi, M. Nakajima and H. Kuwano (2003). "EphA2 overexpression correlates with poor prognosis in esophageal squamous cell carcinoma." *Int J Cancer* 103(5): 657-663.

Mok S C, Bonome T, Vathipadiekal V, Bell A, Johnson M E, et al. (2009) A gene signature predictive for outcome in advanced ovarian cancer identifies a survival factor: microfibril-associated glycoprotein 2. Cancer Cell 16: 521-532.

Morishige, K., H. Kurachi, K. Amemiya, H. Adachi, M. Inoue, A. Miyake, O. Tanizawa and Y. Sakoyama (1991). "Involvement of transforming growth factor alpha/epidermal growth factor receptor autocrine growth mechanism in an ovarian cancer cell line in vitro." *Cancer Res* 51(21): 5951-5955.

Nowsheen, S., T. Cooper, J. A. Bonner, A. F. LoBuglio and E. S. Yang (2012). "HER2 overexpression renders human breast cancers sensitive to PARP inhibition independently of any defect in homologous recombination DNA repair." *Cancer Res* 72(18): 4796-4806.

Owzar K, Barry W T, Jung S H (2011) Statistical Considerations for Analysis of Microarray Experiments. Cts-Clinical and Translational Science 4: 466-477.

Palagani, V., M. El Khatib, U. Kossatz, P. Bozko, M. R. Muller, M. P. Manns, T. Krech, N. P. Malek and R. R. Plentz (2012). "Epithelial mesenchymal transition and pancreatic tumor initiating CD44+/EpCAM+ cells are inhibited by gamma-secretase inhibitor IX." *Plos One* 7(10): e46514.

Perren, T., A. M. Swart, J. Pfisterer, J. Ledermann, A. Lortholary, G. Kristensen, M. Carey, P. Beale, A. Cervantes, A. Oza and G. I. Collaborators (2010). "Icon7: A Phase Iii Randomised Gynaecologic Cancer Intergroup Trial of Concurrent Bevacizumab and Chemotherapy Followed by Maintenance Bevacizumab, Versus Chemotherapy Alone in Women with Newly Diagnosed Epithelial Ovarian (Eoc), Primary Peritoneal (Ppc) or Fallopian Tube Cancer (Ftc)." *Annals of Oncology* 21: 2-3.

Pino, M. S., M. Shrader, C. H. Baker, F. Cognetti, H. Q. Xiong, J. L. Abbruzzese and D. J. McConkey (2006). "Transforming growth factor alpha expression drives constitutive epidermal growth factor receptor pathway activation and sensitivity to gefitinib (Iressa) in human pancreatic cancer cell lines." *Cancer Res* 66(7): 3802-3812.

Rubatt, J. M., K. M. Darcy, A. Hutson, S. M. Bean, L. J. Havrilesky, L. A. Grace, A. Berchuck and A. A. Secord (2009). "Independent prognostic relevance of microvessel density in advanced epithelial ovarian cancer and associations between CD31, CD105, p53 status, and angiogenic marker expression: A Gynecologic Oncology Group study." *Gynecol Oncol* 112(3): 469-474.

Saharinen, P., K. Kerkela, N. Ekman, M. Marron, N. Brindle, G. M. Lee, H. Augustin, G. Y. Koh and K. Alitalo (2005). "Multiple angiopoietin recombinant proteins activate the Tie1 receptor tyrosine kinase and promote its interaction with Tie2." *J Cell Biol* 169(2): 239-243.

Schwartz, J. D., E. K. Rowinsky, H. Youssoufian, B. Pytowski and Y. Wu (2010). "Vascular endothelial growth factor receptor-1 in human cancer: concise review and rationale for development of IMC-18F1 (Human antibody targeting vascular endothelial growth factor receptor-1)." *Cancer* 116(4 Suppl): 1027-1032.

Shibuya, M. (2006). "Vascular endothelial growth factor receptor-1 (VEGFR-1/Flt-1): a dual regulator for angiogenesis." *Angiogenesis* 9(4): 225-230; discussion 231.

Singh, H., T. A. Tahir, D. O. Alawo, E. Issa and N. P. Brindle (2011). "Molecular control of angiopoietin signalling." *Biochem Soc Trans* 39(6): 1592-1596.

Slamon, D. J., B. Leyland-Jones, S. Shak, H. Fuchs, V. Paton, A. Bajamonde, T. Fleming, W. Eiermann, J. Wolter, M. Pegram, J. Baselga and L. Norton (2001). "Use of chemotherapy plus a monoclonal antibody against HER2 for metastatic breast cancer that overexpresses HER2." *New England Journal of Medicine* 344(11): 783-792.

Slungaard, A. (2005). "Platelet factor 4: a chemokine enigma." *Int J Biochem Cell Biol* 37(6): 1162-1167.

Sun, M., G. Wang, J. E. Paciga, R. I. Feldman, Z. Q. Yuan, X. L. Ma, S. A. Shelley, R. Jove, P. N. Tsichlis, S. V. Nicosia and J. Q. Cheng (2001). "AKT1/PKB alpha kinase is frequently elevated in human cancers and its constitutive activation is required for oncogenic transformation in NIH3T3 cells." *American Journal of Patholovgy* 159(2): 431-437.

Takai, N., T. Miyazaki, K. Fujisawa, K. Nasu and I. Miyakawa (2001). "Expression of receptor tyrosine kinase EphB4 and its ligand ephrin-B2 is associated with malignant potential in endometrial cancer." *Oncol Rep* 8(3): 567-573.

Teoh, D. and A. A. Secord (2012). "Antiangiogenic agents in combination with chemotherapy for the treatment of epithelial ovarian cancer." *Int J Gynecol Cancer* 22(3): 348-359.

Tuzi, N. L. and W. J. Gullick (1994). "Eph, the Largest Known Family of Putative Growth-Factor Receptors." *British Journal of Cancer* 69(3): 417-421.

Wang, Z. and H. Huang (2013). "Platelet factor-4 (CXCL4/PF-4): An angiostatic chemokine for cancer therapy." *Cancer Lett.*

Wei, K. C., C. Y. Huang, P. Y. Chen, L. Y. Feng, T. W. Wu, S. M. Chen, H. C. Tsai, Y. J. Lu, N. M. Tsang, C. K. Tseng, P. C. Pai and J. W. Shin (2010). "Evaluation of the prognostic value of CD44 in glioblastoma multiforme." *Anticancer Res* 30(1): 253-259.

Weidner, N., P. R. Carroll, J. Flax, W. Blumenfeld and J. Folkman (1993). "Tumor angiogenesis correlates with metastasis in invasive prostate carcinoma." *Am J Pathol* 143(2): 401-409.

Weidner, N., J. Folkman, F. Pozza, P. Bevilacqua, E. N. Allred, D. H. Moore, S. Meli and G. Gasparini (1992). "Tumor angiogenesis: a new significant and independent prognostic indicator in early-stage breast carcinoma." *J Natl Cancer Inst* 84(24): 1875-1887.

Weidner, N., J. P. Semple, W. R. Welch and J. Folkman (1991). "Tumor angiogenesis and metastasis—correlation in invasive breast carcinoma." *N Engl J Med* 324(1): 1-8.

Wu, Q., Z. Suo, G. B. Kristensen, M. Baekelandt and J. M. Nesland (2006). "The prognostic impact of EphB2/B4 expression on patients with advanced ovarian carcinoma." *Gynecologic Oncology* 102(1): 15-21.

Wu, W., M. S. O'Reilly, R. R. Langley, R. Z. Tsan, C. H. Baker, N. Bekele, X. M. Tang, A. Onn, I. J. Fidler and R. S. Herbst (2007). "Expression of epidermal growth factor (EGF)/transforming growth factor-alpha by human lung cancer cells determines their response to EGF receptor tyrosine kinase inhibition in the lungs of mice." *Mol Cancer Ther* 6(10): 2652-2663.

Yoshihara K, Tajima A, Yahata T, Kodama S, Fujiwara H, et al. (2010) Gene expression profile for predicting survival in advanced-stage serous ovarian cancer across two independent datasets. PLoS One 5: e9615.

Zatterstrom, U. K., E. Brun, R. Willen, E. Kjellen and J. Wennerberg (1995). "Tumor angiogenesis and prognosis in squamous cell carcinoma of the head and neck." *Head Neck* 17(4): 312-318.

Zhang, S., C. Balch, M. W. Chan, H. C. Lai, D. Matei, J. M. Schilder, P. S. Yan, T. H. Huang and K. P. Nephew (2008). "Identification and characterization of ovarian cancer-initiating cells from primary human tumors." *Cancer Res* 68(11): 4311-4320.

Zhang L, Volinia S, Bonome T, Calin G A, Greshock J, et al. (2008) Genomic and epigenetic alterations deregulate microRNA expression in human epithelial ovarian cancer. Proc Natl Acad Sci USA 105: 7004-7009.

Zhao, D., F. Zhang, W. Zhang, J. He, Y. Zhao and J. Sun (2013). "Prognostic role of hormone receptors in ovarian cancer: a systematic review and meta-analysis." *Int J Gynecol Cancer* 23(1): 25-33.

Zoller, M. (2011). "CD44: can a cancer-initiating cell profit from an abundantly expressed molecule?" *Nature Reviews Cancer* 11(4): 254-267.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of predicting survival of a subject having high-grade serous ovarian cancer (HGSC), comprising:
quantifying a gene expression level consisting of an ANGPTL3 biomarker in a biological sample derived from the subject having HGSC comprising one or a combination of ovarian tumor tissue, ovarian tumor cells, or ovarian biopsy tissue relative to a reference control for HGSC subjects including those having a survival of 3 years or less and those having a survival of 7 years or more, wherein the quantifying is carried out by one or a combination of Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array; and
predicting the subject as having the survival of 3 years or less if the gene expression level of the ANGPTL3 biomarker is higher in the biological sample derived from the subject compared to the reference control.

2. The method of claim 1, further comprising administering appropriate ovarian cancer therapy to the subject based on the prediction of the survival of 3 years or less.

3. The method of claim 1, wherein the subject is a mammal.

4. The method of claim 1, wherein the subject is a human.

* * * * *